United States Patent
Segura et al.

(10) Patent No.: US 10,968,281 B2
(45) Date of Patent: Apr. 6, 2021

(54) ANTI-LSP1 ANTIBODY

(71) Applicants: INSTITUT CURIE, Paris (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Elodie Segura, Paris (FR); Sebastian Amigorena, Paris (FR); Franck Perez, Paris (FR); Sandrine Moutel, Paris (FR)

(73) Assignees: INSTITUT CURIE, Paris (FR); CENTRE NATIONAL DE LA RECHERCHE SCIENTIFIQUE, Paris (FR); INSTITUT NATIONAL DE LA SANTÉ ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 16/341,529

(22) PCT Filed: Oct. 13, 2017

(86) PCT No.: PCT/EP2017/076139
§ 371 (c)(1),
(2) Date: Apr. 12, 2019

(87) PCT Pub. No.: WO2018/069480
PCT Pub. Date: Apr. 19, 2018

(65) Prior Publication Data
US 2019/0367635 A1    Dec. 5, 2019

(30) Foreign Application Priority Data
Oct. 14, 2016  (EP) .................................. 16306355

(51) Int. Cl.
| | | |
|---|---|---|
| A61K 39/395 | (2006.01) | |
| A61K 39/00 | (2006.01) | |
| G01N 33/53 | (2006.01) | |
| C07K 16/46 | (2006.01) | |
| C07K 16/00 | (2006.01) | |
| C07K 16/30 | (2006.01) | |
| G01N 33/50 | (2006.01) | |
| A61K 38/00 | (2006.01) | |

(52) U.S. Cl.
CPC ..... *C07K 16/3061* (2013.01); *G01N 33/5008* (2013.01); *A61K 38/00* (2013.01); *C07K 2317/565* (2013.01); *C07K 2317/567* (2013.01); *C07K 2317/569* (2013.01); *G01N 2800/7095* (2013.01)

(58) Field of Classification Search
None
See application file for complete search history.

(56) References Cited

U.S. PATENT DOCUMENTS

| | | | | |
|---|---|---|---|---|
| 7,196,187 | B2 * | 3/2007 | Frenken ............... | C07K 16/00 435/320.1 |
| 2011/0053955 | A1 * | 3/2011 | Abeywardane ...... | C07D 209/42 514/254.02 |
| 2013/0323235 | A1 * | 12/2013 | Craig ................... | C07K 16/00 424/133.1 |

FOREIGN PATENT DOCUMENTS

WO    WO 2015/063331    5/2015

OTHER PUBLICATIONS

Zhang et al. Human Lymphocyte-Specific Protein 1, the Protein Overexpressed in Neutrophil Actin Dysfunction with 47-kDa and 89-kDa Protein Abnormalities (NAD 47/89), Has Multiple F-Actin Binding Domains. The Journal of Immunology, 2000, 165: 2052-2058. (Year: 2000).*

(Continued)

*Primary Examiner* — Maher M Haddad
(74) *Attorney, Agent, or Firm* — Saliwanchik, Lloyd & Eisenschenk

(57) ABSTRACT

The present invention provides a new anti-LSP1 (Leukocyte specific protein 1) antibody. This new antibody allows the specific staining of inflammatory dendritic cells and can be used in diagnosis methods or as a medicament when conjugated to a drug.

22 Claims, 7 Drawing Sheets
Specification includes a Sequence Listing.

(56) References Cited

OTHER PUBLICATIONS

Maxeiner et al. Crucial role for the LSP1-myosin1e bimolecular complex in the regulation of Fcγ receptor-driven phagocytosis. Mol Biol Cell. May 1, 2015;26(9):1652-64. (Year: 2015).*

Huang et al. LSP1 Is the Major Substrate for Mitogen-activated Protein Kinase-activated Protein Kinase 2 in Human Neutrophils. The Journal of Biological Chemistry 272, 17-19, 1997. (Year: 1997).*

Campbell A, General properties and applications of monoclonal antibodies, Elsevier Science Publishers, section 1.1, pp. 1-32, 1984. (Year: 1984).*

Muyldermans et al. Single domain camel antibodies: current status. Reviews in Molecular Biotechnology, vol. 74, p. 277-302, 2001. (Year: 2001).*

Deschacht et al. A Novel Promiscuous Class of Camelid Single-Domain Antibody Contributes to the Antigen-Binding Repertoire. The Journal of Immunology, 2010, 184: 5696-5704. (Year: 2010).*

Khanh et al. Leukocyte-specific protein 1 regulates neutrophil recruitment in acute lung Inflammation. (Am J Physiol Lung Cell Mol Physiol 309: L995-L1008, 2015.) (Year: 2015).*

Pulford, K. et al. "Lymphocyte-specific protein 1: a specific marker of human leucocytes" *Immunology*, 1999, pp. 262-271, vol. 96, No. 2.

Jongstra-Bilen, J. et al. "Leukocyte-Specific Protein 1 (LSP1) *A Regulator of Leukocyte Emigration in Inflammation*" *Immunologic Research*, 2006, pp. 65-73, vol. 35, Nos. 1-2.

Written Opinion in International Application No. PCT/EP2017/076139, dated Jan. 23, 2018, pp. 1-9.

* cited by examiner

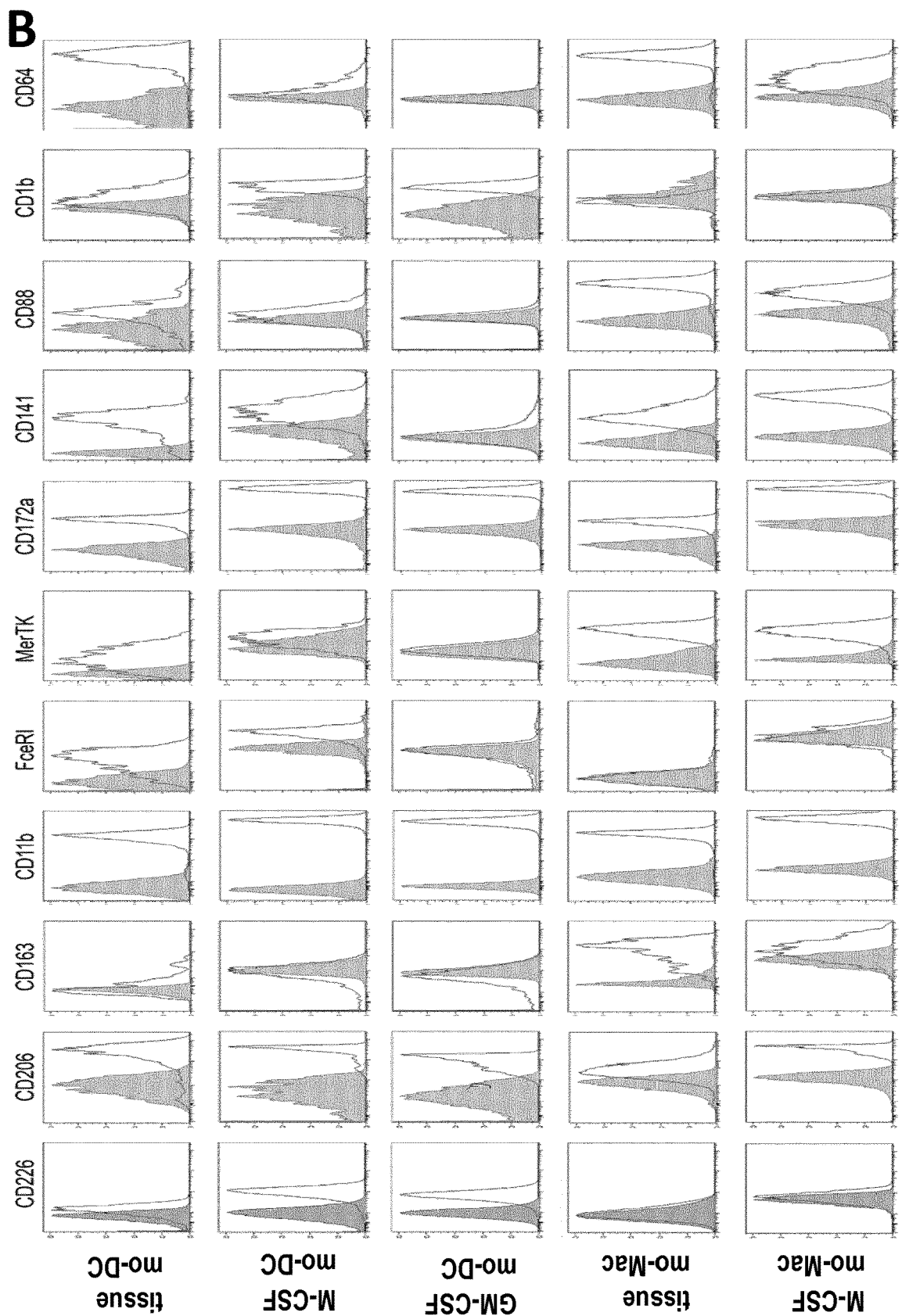
Figure 1 (following)

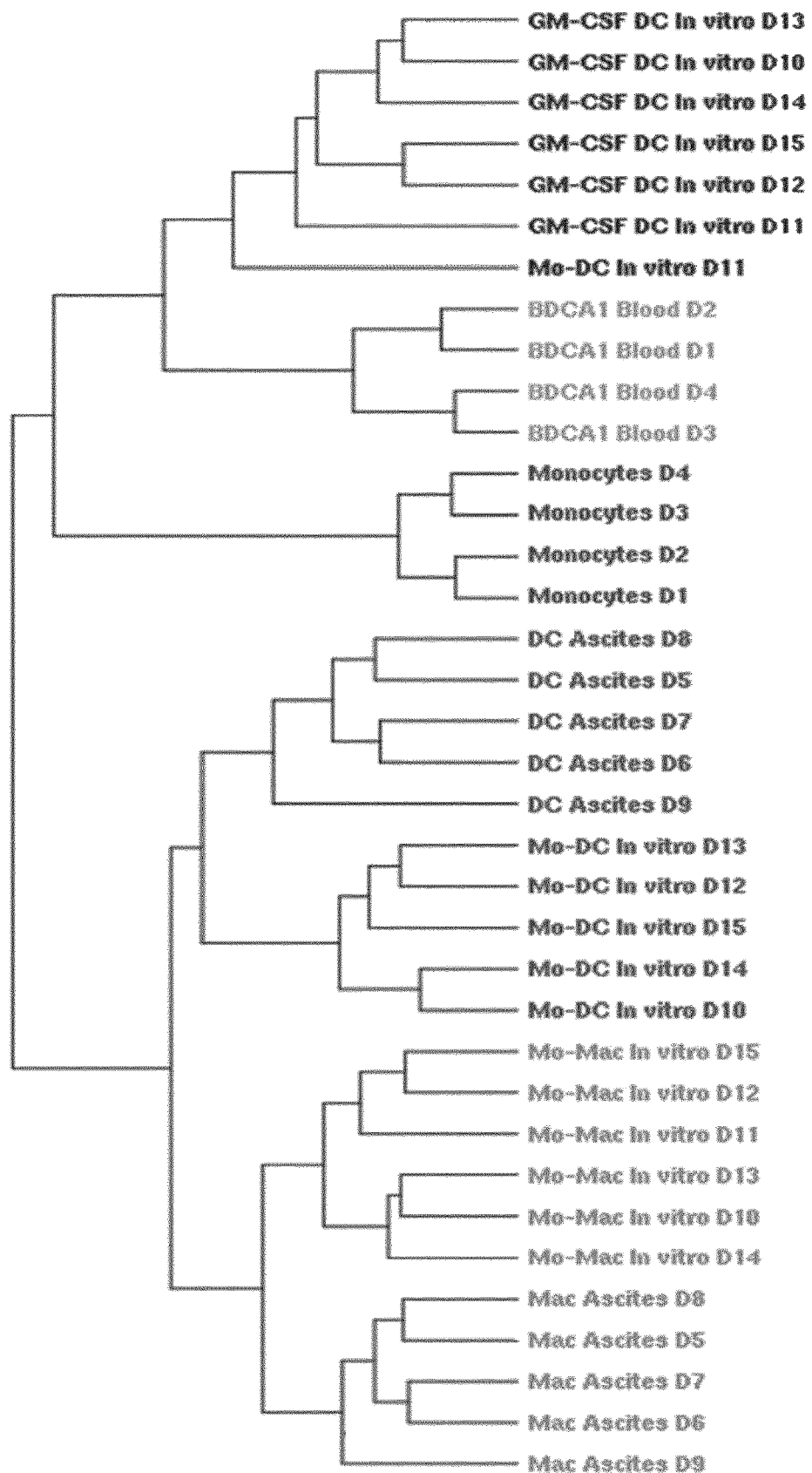
Figure 1 (following)

ANTI-LSP1 ANTIBODY

CROSS-REFERENCE TO RELATED APPLICATION

This application is the U.S. national stage application of International Patent Application No. PCT/EP2017/076139, filed Oct. 13, 2017.

The Sequence Listing for this application is labeled "Seq-List.txt" which was created on Mar. 1, 2019 and is 4 KB. The entire content of the sequence listing is incorporated herein by reference in its entirety.

FIELD OF THE INVENTION

The present invention relates to the field of medicine and research, in particular of inflammatory pathologies. It provides new antibodies to identify inflammatory dendritic cells, new methods for diagnosis of inflammatory pathologies and new treatments of inflammatory pathologies.

BACKGROUND OF THE INVENTION

Inflammation is a physiological response necessary to restore homeostasis altered by diverse stimuli. However, established chronic inflammation state or an excessive inflammatory response can imply deleterious effects, such as in rheumatoid arthritis or inflammatory bowel disease. Chronic inflammation is also considered as a major cause of cancers and aging processes, and has been involved in a wide variety of age-related diseases including diabetes, cardiovascular and autoimmune diseases. Moreover, it has been shown recently that low-grade chronic inflammation is associated with obesity and thus participates actively to the development of obesity associated pathologies. Nowadays, pathological inflammations are therefore a major healthcare issue.

Inflammatory responses are mediated by immune defense cells and associated tissue residential cells that accumulate at the site of tissue injury or trauma to rid of unwanted exogenous agents (e.g., microbes) and endogenous agents (e.g., cancer cell clones), to clean up cellular debris, and to participate in tissue and wound healing. Unfortunately, the molecular mechanisms involved in these reparatory (inflammatory) processes due to, for example, the inappropriate activation of leukocytes, can initiate secondary tissue damages, which, in turn, contribute to the pathogenesis and persistent pathology of several inflammatory and immunomodulatory diseases. The molecular mechanisms and the cellular and chemical mediators involved in secondary tissue damages are similar, if not identical, in most inflammatory diseases.

In the nineties of the past century, a new cytokine, interleukin (IL)-17, was identified (Rouvier E et al, 1993, J Immunol, 150:5445-5456; Yao Z et al, 1995, J Immunol, 155:5483-5486). Subsequently, the presence of a novel T-helper cell subpopulation (Th17), able to produce IL-17, was revealed. Th17 cells are able to produce two isoforms of IL-17, IL-17A and IL-17F (Tesmer L A et al, 2008, Immunol Rev, 223:87-113), which are both pro-inflammatory cytokines. Researchers have shown that IL-17A and/or IL-17F are responsible for development of inflammation in many disorders, especially in autoimmune diseases, like rheumatoid arthritis, psoriasis, juvenile idiopathic arthritis, Crohn's disease as well as in tumor-associated inflammation (Adami S et al, 2014, BioDrugs, 28:487-497; Hot A and Miossec P, 2011, Ann Rheum Dis, 70:727-732; Hu Y et al, 2011, Ann NY Acad Sci, 1217:60-76; Piper C et al, 2014, Arthritis Rheumatol, 66:1955-1960; Tesmer L A et al, 2008, Immunol Rev, 223:87-113; Grivennikov S I et al, 2010, Cell, 140(6): 883-99).

Since the key role of Th17 in inflammatory pathologies has been discovered, many drugs have been developed to target Th17 pathways with a limited success. Indeed, data from phase III clinical trials are moderately encouraging. All the drugs tested insofar are targeting Th17 cells, second messengers downstream of Th17, or some cytokines that are alleged to stimulate TH17 cells such as IL-23, IL-6 or IL-1 (cf. Tabarkiewicz J et al, 2015, Arch. Immunol. Ther. Exp., 63:435-449).

Dendritic cells are antigen-presenting cells which play a critical role in the regulation of the adaptive immune response. Under non-inflammatory conditions, several human dendritic cells subsets have already been identified. Interestingly, the inventors have recently discovered a new dendritic cell population found in human inflammatory fluids and that displays a phenotype distinct from the macrophages present in the same fluids and from steady-state lymphoid organs or blood dendritic cells. They showed that these inflammatory dendritic cells are derived from monocytes, when present on the inflammation site. They also discovered that inflammatory dendritic cells are triggering the differentiation of naive $CD4^+$ T cells into Th17 through the selective secretion of Th17 cell polarizing cytokines (Segura E et al, 2013, Immunity, 38:336-348).

Despite the major role played by this new population of inflammatory dendritic cells in the development of inflammation and in inflammatory pathologies, no efficient tool has been developed yet to allow a specific staining of these inflammatory dendritic cells. Such a tool would be however of major interest not only in fundamental research but also in the diagnosis of inflammatory pathologies. Nowadays, there is also a strong need for new therapies able to efficiently block the Th17 inflammatory pathway. The present invention seeks to meet these and other needs.

SUMMARY OF THE INVENTION

The inventors have discovered a new antibody that specifically stains inflammatory dendritic cells. Indeed, this new antibody is able to stain inflammatory dendritic cells but do not stains inflammatory macrophages (which are derived from the same monocyte lineage), blood monocytes or other populations of human dendritic cells. The inventors have surprisingly discovered that the antibody of the invention binds to the leukocyte specific protein 1 (LSP1), a protein which is known to be intracellular but is, at least partially, expressed at the membrane of inflammatory dendritic cells. On the opposite, a commercial anti-LSP1 antibody was unable to stain the same inflammatory dendritic cells, underlying the key importance of the epitope recognized by the anti-LSP1 antibody of the invention in the specific staining of inflammatory dendritic cells.

Accordingly, in a first aspect, the present invention concerns an anti-LSP1 (Leukocyte specific protein 1) antibody comprising a variable domain that comprises three CDRs (complementarity determining regions) consisting or consisting essentially in the amino acid sequences of SEQ ID NO: 1, SEQ ID NO: 2 and SEQ ID NO: 3, or any antibody capable to compete with said anti-LSP1 antibody for the binding to LSP1.

Preferably, the anti-LSP1 antibody according to the invention is a single domain antibody, preferably a humanized single domain antibody, or a fragment thereof.

In a preferred embodiment, the variable domain of the anti-LSP1 antibody according to the invention comprises the sequence FR1-CDR1-FR2-CDR2-FR3-CDR3-FR4, wherein FR1, FR2, FR3 and FR4 are framework regions, preferably humanized framework regions, of a VHH, preferably from Camelidae, more preferably from Llama species, or camelized framework regions of a human VH.

Preferably, in the variable domain of the anti-LSP1 antibody according to the invention:
- CDR1 consists or consists essentially in an amino acid sequence of SEQ ID NO:1;
- CDR2 consists or consists essentially in an amino acid sequence of SEQ ID NO: 2; and
- CDR3 consists or consists essentially in an amino acid sequence of SEQ ID NO: 3.

Preferably, in the variable domain of the anti-LSP1 antibody according to the invention:
- FR1 consists or consists essentially in an amino acid sequence having at least 50%, 60%, 70%, 80%, 90%, 95%, sequence identity with the sequence of SEQ ID NO: 4, preferably FR1 has the amino acid sequence of SEQ ID NO: 4;
- FR2 consists or consists essentially in an amino acid sequence having at least 50%, 60%, 70%, 80%, 90%, 95%, sequence identity with the sequence of SEQ ID NO: 5, preferably FR2 has the amino acid sequence of SEQ ID NO: 5;
- FR3 consists or consists essentially in an amino acid sequence having at least 50%, 60%, 70%, 80%, 90%, 95%, sequence identity with the sequence of SEQ ID NO: 6, preferably FR3 has the amino acid sequence of SEQ ID NO: 6; and/or
- FR4 consists or consists essentially in an amino acid sequence having at least 50%, 60%, 70%, 80%, 90%, 95%, sequence identity with the sequence of SEQ ID NO: 7, preferably FR4 has the amino acid sequence of SEQ ID NO: 7.

In a particularly preferred embodiment, the anti-LSP1 antibody according to the invention is an antibody that comprises, consists in, or consists essentially in, the amino acid sequence of SEQ ID NO: 8 or a variant amino acid sequence having no more than 1, 2, 3, 4, 5, 6, 7, 8, 9, or 10 amino acid additions, deletions, substitutions, or combinations thereof within the sequence of SEQ ID NO: 8, or is any antibody capable to compete with said anti-LSP1 antibody for the binding to LSP1.

In a particular embodiment, the anti-LSP1 antibody according to the invention is labelled or fused to a detection entity, preferably the anti-LSP1 antibody is labelled, even more preferably the anti-LSP1 antibody according to the invention is labelled with a fluorescent label.

The present invention also concerns, in a second aspect, the use of an anti-LSP1 antibody according to the invention as a research tool, in particular for specific binding, for purification, for immuno-staining, or for in-vivo imaging of inflammatory dendritic cells.

In a third aspect, the invention also concerns the use of an anti-LSP1 antibody according to the invention as a diagnosis marker, in particular for inflammatory pathologies, for selecting a subject for a treatment with an anti-inflammatory drug, or for predicting the efficacy of a treatment with an anti-inflammatory drug in a subject.

The present invention yet concerns, in a fourth aspect, an in vitro method for diagnosing inflammatory pathologies in a subject, for selecting a subject for a treatment with an anti-inflammatory drug or for predicting the efficacy of a treatment with an anti-inflammatory drug in a subject, wherein the method comprises a step of staining inflammatory dendritic cells in a biological sample from said subject with an anti-LSP1 antibody according to the invention.

In a preferred embodiment, the anti-LSP1 antibody according to the invention is conjugated to a drug or to an antigen, in particular a cancer antigen. Preferably, the anti-LSP1 antibody according to the invention is conjugated to a drug, more preferably to a cytotoxic drug or an anti-inflammatory drug, even more preferably a cytotoxic drug.

In a fifth embodiment, the invention still concerns an anti-LSP1 antibody conjugated to a drug or to an antigen according to the invention for use as a medicament.

The invention also concerns, in a sixth embodiment, a pharmaceutical composition comprising an anti-LSP1 antibody conjugated to a drug or to an antigen according to the invention and at least one pharmaceutically acceptable excipient.

In a seventh embodiment, the invention finally concerns the antibody according to the invention or the pharmaceutical composition according to the invention for use in the treatment of inflammatory pathologies.

Bands were excised and corresponding proteins sequenced by mass spectrometry. MW=molecular weight. (B-C) After incubation with D4, in vitro equivalents of inflammatory macrophages (Macro) or dendritic cells (DC) were lysed and immunoprecipitation was performed on cell lysate by immuno-precipitating the C-terminal tag. Immuno-precipitated material was loaded on a gel. After migration, proteins were transferred on a membrane. Western Blot analysis was performed using streptavidin-HRP (B) or a commercial anti-LSP-1 antibody (C). MW=molecular weight.

Figure 4:
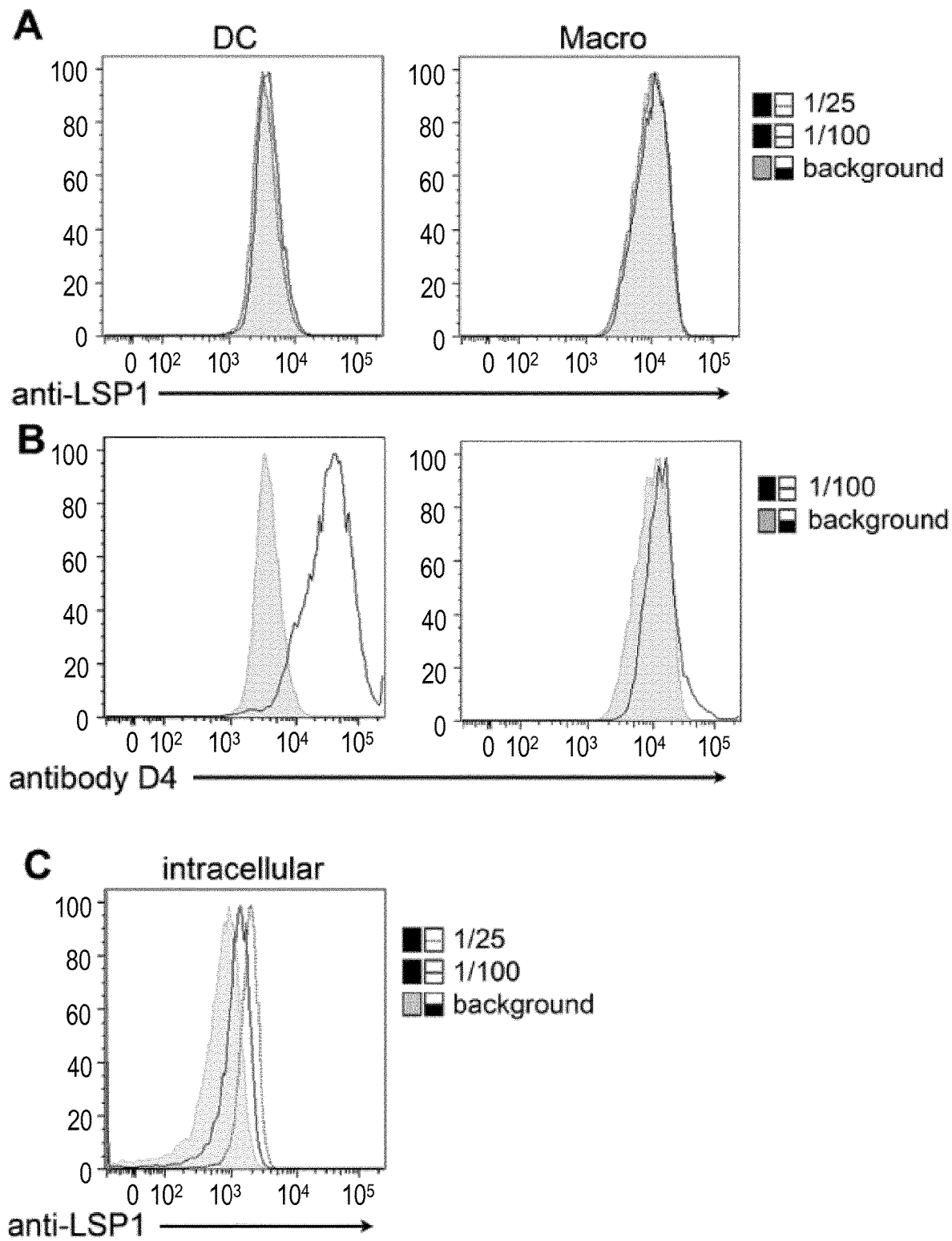

FIG. 4: Commercially available polyclonal anti-LSP1 does not stain inflammatory DC extracellularly. (A-B) In vitro equivalents of inflammatory DC and macrophages were derived in vitro from monocytes. Cells were stained with several dilutions of commercial anti-LSP1 antibody (A) (initial concentration: 0.9 mg/mL), or with antibody D4 (B). (C) In vitro equivalents of inflammatory DC were fixed and permeabilized, then stained with several dilutions of commercial anti-LSP1 antibody.

Figure 5:
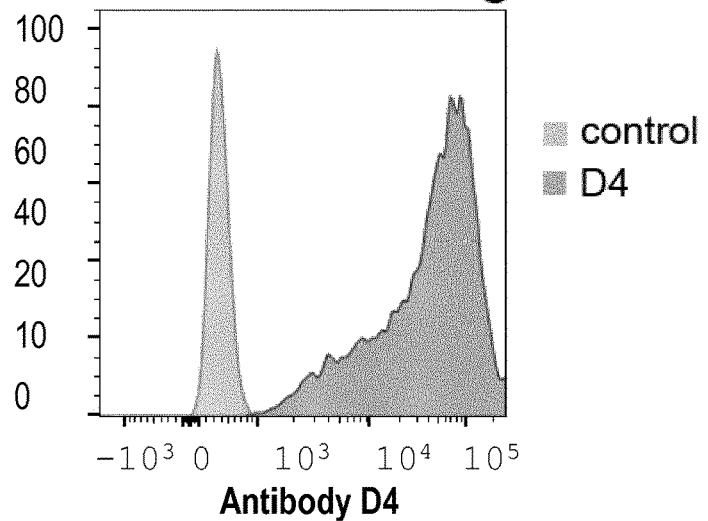
Figure 5:
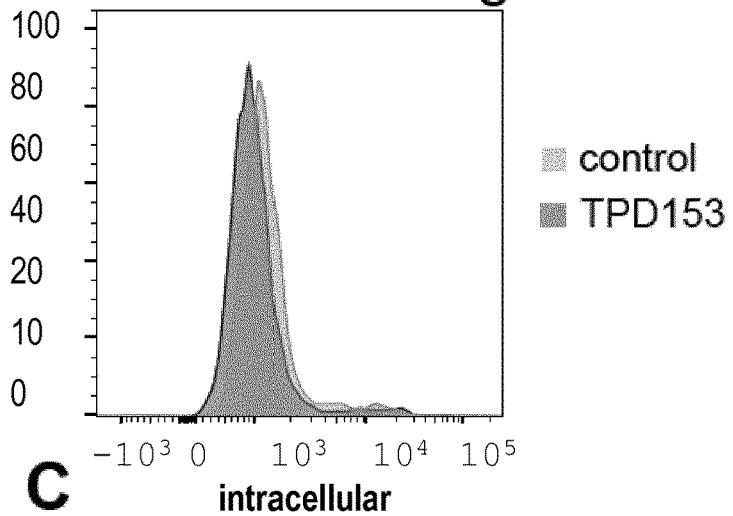
Figure 5:
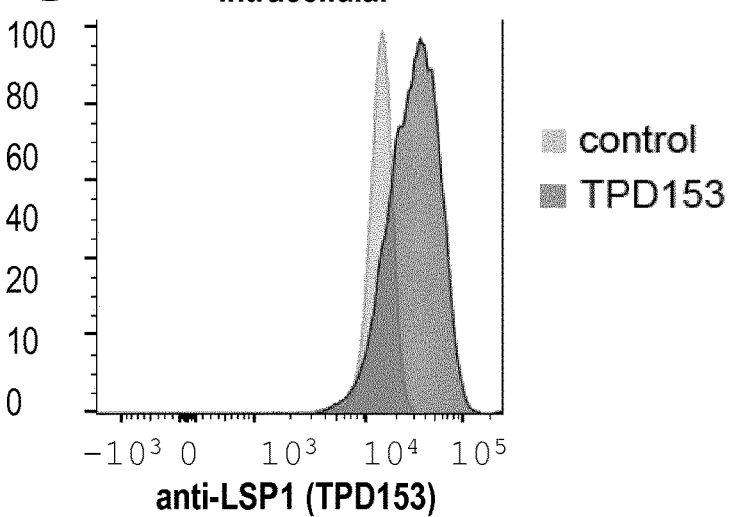

FIG. 5: Commercially available polyclonal anti-LSP1 TPD153 does not stain inflammatory DC extracellularly. (A-B) In vitro equivalents of inflammatory DC were derived in vitro from monocytes. Cells were stained with commercial anti-LSP1 antibody TPD153 (B) (concentration: 6.5 µg/mL), or with antibody D4 (concentration 5 µg/mL) (A). (C) In vitro equivalents of inflammatory DC were fixed and permeabilized, then stained with commercial anti-LSP1 antibody TPD153.

DETAILED DESCRIPTION OF THE INVENTION

The inventors have discovered a new antibody that specifically stains human inflammatory dendritic cells, thereby providing the first specific tool allowing to identify inflammatory dendritic cells in humans. Indeed, this new antibody is able to stain inflammatory dendritic cells without any cross-staining of inflammatory macrophages, a population that also differentiates from monocytes in inflammatory environments, blood monocytes or other populations of human dendritic cells. The inventors have discovered that the antibody of the invention binds to the leukocyte specific protein 1 (LSP1), a protein which is known to be expressed only intracellularly in lymphocytes, neutrophils, macrophages, and endothelium. However, LSP1 appears to be, at least partially, expressed at the membrane of inflammatory dendritic cells since non-permeabilized inflammatory dendritic cells are stained by this antibody. On the opposite, a commercial anti-LSP1 antibody was totally unable to stain non-permeabilized inflammatory dendritic cells, pointing out the unique technical properties of the anti-LSP1 antibody of the invention.

Definitions

As used herein, the terms "dendritic cell" or "classical dendritic cells" are equivalent and refer to a population of antigen-presenting cells of the mammalian immune system that can be identified by the combination of the following markers in humans: CD3−CD19−CD56−CD11c+HLADR+ CD14−CD16−. The dendritic cells are classically divided into 2 main subsets expressing BDCA1/CD1c or BDCA3/CD141.

As used herein, the term "inflammatory dendritic cells" refers to a population of antigen-presenting cells of the mammalian immune system that differentiate from monocyte in the context of an inflammatory environment and that can be identified by the following combination of markers in humans: CD3−CD19−CD56−CD11c+HLADR+CD14+ CD16−CD1c+.

As used herein, the term "inflammatory macrophages" refers to a population of macrophages that that differentiate from monocyte in the context of an inflammatory environment and that can be identified by the following combination of markers in humans: CD3−CD19−CD56−CD11c+ HLADR+CD14+CD16+CD1c−.

As used herein, the terms "leukocyte specific protein 1", "lymphocyte specific protein 1", "LSP1", "Lymphocyte-Specific Antigen WP34", "47 KDa Actin-Binding Protein", "52 KDa Phosphoprotein", "WP34", "Pp52", "F-Actin Binding And Cytoskeleton Associated Protein 3", "Leufactin (Leukocyte F-Actin Binding Protein) 3", "47 KDa Actin Binding Protein 3" are equivalent and can be used one for the other. LSP1 is an intracellular F-actin binding cytoskeletal protein (human LSP1 UniProtKB: P33241) expressed in hematopoietic lineage and endothelial cells.

As used herein, the terms "antibody" refers to immunoglobulin molecules and immunologically active portions of immunoglobulin molecules, i.e., molecules that contain an antigen-binding site that immunospecifically binds an antigen. As such, the term antibody encompasses not only whole antibody molecules, but also antigen-binding antibody fragments as well as variants (including derivatives) of antibodies and antibody fragments. In particular, the antibody according to the invention may correspond to a monoclonal antibody (e.g. a chimeric, humanized or human antibody), or a fragment of monoclonal antibody. The term antibody refers to classical antibodies as well as to Heavy-chain antibodies and fragments and derivatives thereof such $(VHH)_2$ fragments and single domain antibodies.

As used herein, the term "classical antibody" refers to a large Y-shaped glycoprotein that is typically made of two large heavy-chains linked to each other by disulfide bonds, each heavy chain being linked to a small light-chain by a disulfide bond. Each chain is composed of structural domains, i.e. immunoglobulin domains. These domains contain about 70-110 amino acids and are classified into variable (IgV), and constant (IgC) domains. Antibodies are capable to recognize a unique molecule, i.e. an antigen, an epitope or a ligand, via its variable regions located at the tip of the "Y" of a classical antibody. In placental mammals there are five classical antibody isotypes known as IgA, IgD, IgE, IgG, and IgM that are classified according to the type of their heavy chains denoted by the Greek letters: α, δ, ε, γ, and µ respectively. Classical antibodies can polymerized, in particular to form dimers or pentamers.

As used herein, the term "heavy chain" refers to a polypeptide constituted of two regions, the constant region formed of three or four immunoglobulin constant domains depending on the type of heavy chain and the variable region formed of a single immunoglobulin variable domain.

As used herein, the term "light chain" refers to a polypeptide constituted of two regions, the constant region formed of a single immunoglobulin constant domains and the variable region formed of a single immunoglobulin variable domain. In mammals there are two types of immunoglobulin light chain, which are called lambda (λ) and kappa (κ).

As used herein the term "variable domain" refers to the immunoglobulin domain of a heavy or of a light chain that is responsible for binding to an antigen. A variable domain comprise several loops referred to as hypervariables or Complementary determining region (CDRs) which are responsible for binding to the antigen.

As used herein "VH" refers to the variable domain of a heavy chain.

As used herein, the term "Fc (Fragment, crystallizable) region" refers to the part of the heavy chain corresponding to the first two or three immunoglobulin constant domain (depending on the type of heavy chain) present at the base of the "Y" in a classical antibody. The Fc region contains a conserved glycosylation site involved in different interactions.

An "antibody fragment" of classical antibodies comprises a portion of an intact antibody, preferably the antigen binding or variable region of the intact antibody. Examples of antibody fragments include Fv, Fab, Fab', F(ab)$_2$, F(ab')$_2$, F(ab)$_3$, Fv (typically the VL and VH domains of a single arm of an antibody), single-chain Fv (scFv), di-scFvs or sc(Fv)$_2$, dsFv, Fd (typically the VH and CH1 domain), dAb (typically a VH domain), CDRs, VH, VL, minibodies, diabodies and multi-specific antibodies formed from antibodies fragments.

The term "Fab" denotes an antibody monovalent fragment having a molecular weight of about 50,000 and antigen binding activity, and consisting of the light and heavy chains variable domains (VL and VH), the light chain constant domain (CL) and the first heavy chain constant domain (CH1) domains which can be obtained by cutting a disulfide bond of the hinge region of the F(ab')2 fragment.

The term "Fv" refers to the N-terminal part of the Fab fragment and consists of the variable portions of a light chain and a heavy chain.

The term "F(ab')$_2$" refers to an antibody bivalent fragment having a molecular weight of about 100,000 and antigen binding activity, which comprises two Fab fragments linked by a disulfide bridge at the hinge region.

The term "Fd" refers to an antibody fragment consisting of the VH and CH1 domains.

The term "dAb" (Ward et al., 1989 Nature 341:544-546) refers to a single variable domain antibody, i.e. an antibody fragment which consists of a VH or VL domain.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs such as di-scFvs, or can be generated by coupling monovalent scFvs by a peptide linker, such as divalent sc(Fv)$_2$.

The term "diabodies" refers to small antibody fragments with two antigen-binding sites, which fragments comprise a VH domain connected to a VL domain in the same polypeptide chain (VH-VL). By using a linker that is too short to allow pairing between the two domains on the same chain, the domains are forced to pair with the complementarity domains of another chain and create two antigen-binding sites. The diabody may be mono- or bi-specific.

Antibody fragments which recognize specific epitopes can be generated by known techniques. The antibody fragments are antigen binding portions of an antibody, such as F(ab')$_2$, Fab, Fv, scFv and the like. Other antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

As used herein, the terms "Heavy-chain antibody" or "HCAbs" refer to immunoglobulins which are devoid of light chains and consist in two heavy chains. These antibodies do not rely upon the association of heavy and light chain variable domains for the formation of the antigen-binding site but instead the variable domain of the heavy polypeptide chains alone naturally forms the complete antigen binding site. Each heavy chain comprises a constant region and a variable domain which enables the binding to a specific antigen, epitope or ligand. As used herein, HCAbs encompass heavy chain antibodies of the camelid-type in which each heavy chain comprises a variable domain called VHH and two constant domains. Such heavy-chain antibodies directed against a specific antigen can be obtained from immunized camelids. Camelids encompass dromedary, camel, lama and alpaca. Camelid HCAbs have been described by Hamers-Casterman et al., *Nature*, 1993, 363: 446. Other examples of HCAb are immunoglobulin-like structures (Ig-NAR) from cartilaginous fishes. Heavy-chain antibodies can be humanized using well-known methods.

The terms "single domain antibody", "sdAb" and "nanobody" are used interchangeably and have the same meaning. As used herein, the term single domain antibody refers to a single variable domain derived from a heavy chain antibody, which is able to bind an antigen, an epitope or a ligand alone, that is to say, without the requirement of another binding domain. A single domain antibody may be or may derive from VHH and V-NAR. V-NAR refers to the variable domain found in immunoglobulin-like structures (Ig-NAR) discovered in cartilaginous fishes such as sharks. As an alternative, single domain antibody may be obtained from human VH by camelization, in particular with F37, E44, R45 and F47 mutations. For review about single domain antibodies, one may refer to Saerens et al., *Current Opinion in Pharmacology*, 2008, 8:600-608, the disclosure of which being incorporated by reference. In a preferred embodiment, the single domain antibody according to the invention is a synthetic single domain antibody.

As used herein, the term "synthetic" means that such antibody has not been obtained from fragments of naturally occurring antibodies but produced from recombinant nucleic acids comprising artificial coding sequences (cf. WO 2015/063331).

The term "VHH", as used herein, refers to an antibody fragment consisting of the VH domain of camelid heavy-chain antibody. VHH fragments can be produced through recombinant DNA technology in a number of microbial hosts (bacterial, yeast, mould), as described in WO 94/29457. Alternatively, binding domains can be obtained by modification of the VH fragments of classical antibodies by a procedure termed "camelization", described by Davies et al, 1995. Dimers of VHH fragments, i.e. (VHH)$_2$, can be generated by fusing two sequences encoding VHH fragments, end to end, e.g. by PCR. Preferably, the (VHH)$_2$ fragment is monospecific. The two VHH of a (VHH)$_2$ may also recognize two different antigen, i.e. the (VHH)$_2$ may be bispecific.

The variable domain of an antibody of the invention comprises at least three complementarity determining region (CDR) which determines its binding specificity. Preferably, in a variable domain, the CDRs are distributed between framework regions (FRs). The variable domain thus contains at least 4 framework regions interspaced by 3 CDR regions, resulting in the following typical antibody variable domain structure: FR1-CDR1-FR2-CDR2-FR3-CDR3-FR4. CDRs and/or FRs of the single domain antibody of the invention may be fragments or derivatives from a naturally-occurring antibody variable domain or may be synthetic.

A "humanized antibody" is a chimeric, genetically engineered, antibody in which the CDRs from an antibody, e.g. a mouse antibody (donor antibody), are grafted onto a human antibody (acceptor antibody). Thus, a humanized antibody is an antibody having CDRs from a donor antibody and variable region framework and constant regions, when present, from a human antibody.

Likewise, a "camelized antibody" is an antibody having CDRs from a donor antibody, preferably a human donor, and variable region framework and constant regions, when present, from a Camelid antibody.

The term "monoclonal antibody" or "mAb" as used herein refers to an antibody molecule of a single amino acid composition, that is directed against a specific antigen and which may be produced by a single clone of B cells or hybridoma, or by recombinant methods. The use of antibody components derived from humanized monoclonal antibodies obviates potential problems associated with the immunogenicity of murine constant regions. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)).

Antibodies according to the invention may be produced by any technique known in the art, such as, without limitation, any chemical, biological, genetic or enzymatic technique, either alone or in combination. The antibodies of the invention can be obtained by producing and culturing hybridomas. See also WO 2015/063331 for the production of synthetic single domain antibodies.

As used herein, the terms "sequence identity" or "identity" are used interchangeably and refer to an exact amino acid to amino acid correspondence of two amino acid sequences. Percent of identity between two amino acid sequences (A) and (B) is determined by comparing the two sequences aligned in an optimal manner, through a window of comparison. Said alignment of sequences can be carried out by well-known methods, for example, using the algorithm for global alignment of Needleman-Wunsch. Protein analysis software matches similar sequences using measures of similarity assigned to various substitutions, deletions and other modifications, including conservative amino acid substitutions. Once the total alignment is obtained, the percentage of identity can be obtained by dividing the full number of identical amino acid residues aligned by the full number of residues contained in the longest sequence between the sequence (A) and (B). Sequence identity is typically determined using sequence analysis software. For comparing two amino acid sequences, one can use, for example, the tool "Emboss needle" for pairwise sequence alignment of proteins providing by EMBL-EBI and available on (see Worldwide Website: ebi.ac.uk/Tools/services/web/toolform.ebi?tool=emboss_needle&context=protein), using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

As used herein, the terms "Amino acid modification", "amino acid change", and "mutation" are used interchangeably and refer to a change in an amino acid sequence such as a substitution, an insertion, and/or a deletion.

By "amino acid substitution" or "substitution" herein is meant the replacement of an amino acid at a particular position in a parent amino acid sequence with another amino acid.

By "amino acid insertion" or "insertion" is meant the addition of an amino acid at a particular position in a parent amino acid sequence.

By "amino acid deletion" or "deletion" is meant the removal of an amino acid at a particular position in a parent amino acid sequence.

The amino acid substitutions may be conservative. A conservative substitution is the replacement of a given amino acid residue by another residue having a side chain ("R-group") with similar chemical properties (e.g., charge, bulk and/or hydrophobicity). In general, a conservative amino acid substitution will not substantially change the functional properties of a protein. Conservative substitutions and the corresponding rules are well-described in the state of the art. For instance, conservative substitutions can be defined by substitutions within the groups of amino acids reflected in the following tables:

TABLE 1

Amino Acid Residue

| Amino Acid groups | Amino Acid Residues |
| --- | --- |
| Acidic Residues | ASP and GLU |
| Basic Residues | LYS, ARG, and HIS |
| Hydrophilic Uncharged Residues | SER, THR, ASN, and GLN |
| Aliphatic Uncharged Residues | GLY, ALA, VAL, LEU, and ILE |
| Non-polar Uncharged Residues | CYS, MET, and PRO |
| Aromatic Residues | PHE, TYR, and TRP |

TABLE 2

Alternative Conservative Amino Acid Residue Substitution Groups

| 1 | Alanine (A) | Serine (S) | Threonine (T) |
| --- | --- | --- | --- |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) |
| 6 | Phenylalanine (F) | Tyrosine (Y) | Tryptophan (W) |

TABLE 3

Further Alternative Physical and Functional Classifications of Amino Acid Residues

| | |
| --- | --- |
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | E, Q, T, K, S, G, P, D, E, and R |

Additional groups for conservative substitutions are: valine-leucine-isoleucine, phenylalanine-tyrosine, lysine-arginine, alanine-valine, and asparagine-glutamine.

As used herein, the terms "parent amino acid sequence" or "parent polypeptide" are equivalent and refer to an unmodified amino acid sequence that is subsequently modified to generate a variant. In the context of the invention, the parent amino acid sequence may be a variable domain, a CDR or a FR.

As used herein, the term "consists essentially in" is intended to refer to an amino acid sequence that differs from that of a parent amino acid sequence by virtue of 1, 2, or 3 substitutions, additions, deletions or combination thereof.

As used herein, the terms "variant amino acid sequence", variant polypeptide" or "variant" are equivalent and refer to an amino acid sequence that differs from that of a parent amino acid sequence by virtue of at least one amino acid modification. In the context of the invention, a variant is a variant of a variable domain, a CDR or a FR. Typically, a variant comprises from 1 to 40 amino acid modifications, preferably from 1 to 30 amino acid modifications, more preferably 1 to 20 amino acid modifications. In particular, the variant may have from 1 to 15 amino acid changes, e.g. 1, 2, 3, 4, 5, 6, 7, 8, 9, 10, 11, 12, 13, 14, 15 amino acid changes as compared to its parent amino acid sequence. In a specific aspect, the variant may have from 1 to 3 amino acid changes, e.g. 1, 2, or 3 amino acid changes as compared to its parent amino acid sequence. The variants may comprise one or several amino acid substitutions, and/or, one or several amino acid insertions, and/or one or several amino acid deletions. In some embodiments, the variant may comprise one or several conservative substitutions, e.g. as shown here above. In some other embodiments, the variant comprises one or several amino acid modifications in the framework domains.

The term "label", as used herein, refers to any atom or molecule that can be used to provide a quantifiable signal and that can be attached to an anti-LSP1 antibody of the invention via a covalent bond or a noncovalent interaction (e.g., through ionic or hydrogen bonding, or via immobilization, adsorption, or the like). A label according to the invention may be selected from the group consisting in a radiolabel, an enzyme label, a fluorescent label, a biotin-avidin label, a chemiluminescent label, and the like. Preferably, the label is fused at the C-terminal extremity of the protein.

The term detection "entity", as used herein, refers to an amino acid sequence that form a fusion protein with an anti-LSP1 antibody of the invention and that provide a quantifiable signal. A detection entity according to the invention may be selected from the group consisting in a tag, an enzyme or a fluorescent protein. Preferably, the detection entity is fused at the C-terminal extremity of the protein.

As used herein, the term "fusion protein" or "chimeric protein" are equivalent and refers to protein created through the joining of two or more genes that originally coded for separate proteins. Translation of this fusion gene results in a single polypeptide with functional properties derived from each of the original proteins. Preferably, the fusion protein of the invention is a recombinant fusion proteins created artificially by recombinant DNA technology.

As used herein the term "inflammatory pathologies" refers to any established chronic inflammation state or to any excessive inflammatory response that can involve deleterious effects. In particular, the term "inflammatory pathologies" encompasses chronic inflammatory pathologies, autoimmune diseases, auto-inflammatory diseases, allergies and cancers. Preferably, the inflammatory pathology of the invention is an inflammatory pathology involving Th17, i.e. Th17 cells are present in the environment of the inflammation.

Preferably, the inflammatory pathology is selected from the group consisting in rheumatoid arthritis, juvenile idiopathic arthritis, asthma, inflammatory bowel diseases such as Crohn's disease and ulcerative colitis, tumor ascites, psoriasis, acne vulgaris, atopic dermatitis, chronic non-healing skin ulcers, photoaging (skin aging), systemic lupus erythematosus, granuloma, chronic gastritis, chronic prostatitis, diverticulitis, interstitial cystitis, glomerulonephritis, celiac disease, chronic obstructive pulmonary disease, pelvic inflammatory disease, vasculitis, periodontitis, advanced atherosclerosis, encephalomyelitis, Sjögren syndrome, multiple sclerosis, myasthenia gravis, systemic sclerosis, primary sclerosing cholangitis, ankylosing spondylitis, rheumatic fever, aneurysm (abdominal, thoracic, cerebral), sarcoidosis, hidradenitis suppurativa, chronic inflammations induced by a bacteria such as bacteria of the genus *Mycobacterium*, in particular in granuloma of subjects suffering from tuberculosis or in lesions of subjects suffering from leprosy, hypersensitivities, type 1 diabetes, autoimmune thyroid disorders such as Graves' disease and Hashimoto's disease, reperfusion injury, and transplant rejection, even more preferably the inflammatory pathology is selected from the group consisting in rheumatoid arthritis, juvenile idiopathic arthritis, asthma, inflammatory bowel diseases such as Crohn's disease and ulcerative colitis, tumor ascites, and psoriasis.

As used herein, the term 'inflammation" refers to a complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Classical signs of acute inflammation are calor, dolor, rubor, tumor (heat, pain, redness and swelling) and loss of function. Too little inflammation could lead to progressive tissue destruction by the harmful stimulus (e.g. bacteria) and compromise the survival of the organism. In contrast, chronic inflammation may lead to a host of diseases. Inflammation is therefore normally closely regulated by the body.

As used herein, the term "acute inflammation" refers to the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue.

As used herein the term "chronic inflammation" refers to a prolonged inflammation that leads to a progressive shift in the type of cells present at the site of inflammation, such as mononuclear cells, and is characterized by simultaneous destruction and healing of the tissue from the inflammatory process.

As used herein, the term "chronic inflammatory pathology" refers to a pathology driven by a chronic inflammation.

As used herein, the term "autoimmune disease" refers to a pathological state arising from an abnormal immune response of the body to substances and tissues that are normally present in the body.

As used herein, the term "autoinflammatory disease" refers to a pathological state arising when the innate immune system causes inflammation for unknown reasons.

As used herein, the term "allergy" refers to conditions caused by Hypersensitivity of the immune system to something in the environment that usually causes little or no problem in most people.

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. In particular, the term encompasses prostate cancer at any stage of progression.

As used herein, the term "T helper 17 lymphocytes" or "Th17" are equivalent and refers to a class of lymphocytes that differentiate from $CD4^+$ T lymphocytes in the context of an inflammatory environment. T helper 17 lymphocytes synthetize two pro-inflammatory cytokines: IL-17A and IL-17F.

As used herein, the term "diagnosis" refers to the determination as to whether a subject is likely to be affected of an inflammatory pathology. The skilled artisan often makes a diagnosis on the basis of one or more diagnosis markers, the presence, absence, or amount of which being indicative of the presence or absence of the inflammatory pathology. By "diagnosis" is also intended to refer to the providing of information useful for diagnosis.

As used herein, the term "diagnosis marker" and "biomarker" are interchangeable and refer to biological parameters that aid the diagnosis of an inflammatory pathology or a cancer. It is a measurable indicator of the presence of this disease. This term refers particularly to "inflammatory pathology diagnosis markers" and "tumor diagnosis markers".

The terms "quantity," "amount," and "level" are used interchangeably herein and may refer to an absolute quantification of a molecule in a sample, or to a relative quantification of a molecule in a sample, i.e., relative to another value such as relative to a reference value as taught herein.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

As used herein, the terms "subject", "individual" or "patient" are interchangeable and refer to an animal, preferably to a mammal, even more preferably to a human. However, the term "subject" can also refer to non-human animals, in particular mammals such as dogs, cats, horses, cows, pigs, sheep and non-human primates, among others.

As used herein, the terms "active principle", "active ingredient" "active pharmaceutical ingredient" and "therapeutic agent" are equivalent and refers to a component of a pharmaceutical composition having a therapeutic effect.

As used herein, the term "therapeutic effect" refers to an effect induced by an active ingredient or by a pharmaceutical composition according to the invention, capable to prevent or to delay the appearance of an inflammatory pathology, or to cure or to attenuate the effects of an inflammatory pathology.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

As used herein, the term "effective amount" refers to a quantity of an active ingredient or of a pharmaceutical composition which prevents, removes or reduces the deleterious effects of the disease.

As used herein, the term "expression cassette" refers to a nucleic acid construction comprising a coding region and regulatory regions necessary for expression, operably linked to the coding region. The expression "operably linked" indicates that the elements are combined in such a way that the expression of the coding region is under the control of the regulatory regions. Typically, a regulatory region is located upstream of the coding region at a distance compatible with the control of its expression. The regulatory region can include promoters, enhancers, silencers, attenuators, and internal ribosome entry sites (IRES). Spacer sequences may also be present between regulatory elements and the coding region, as long as they don't prevent its expression. An expression cassette may also include a start codon in front of a protein-encoding gene, splicing signals for introns, and stop codons, transcription terminators, polyadenylation sequences.

As used herein, the terms "promoter" and "transcriptional promoter" are equivalent and refer to a region of DNA that is part of the regulatory region of an expression cassette. The promoter is the regulatory element that initiates the transcription of a particular gene. Promoters are located near the transcription start site of genes, on the same strand and upstream on the DNA (towards the 5' region of the sense strand).

As used herein, the term "vector" refers to a nucleic acid molecule, typically DNA or RNA that serves to transfer a passenger nucleic acid sequence, i.e. DNA or RNA, into a host cell. A vector may comprise an origin of replication, a selectable marker, and a suitable site for the insertion of a gene such as the multiple cloning site. There is several common types of vectors including plasmids, phages, phagemids, viruses, cosmids, and artificial chromosomes.

As used herein, the term "expression vector" refers to a vector designed for gene expression in cells. An expression vector allow to introduce a specific gene into a target cell, and can commandeer the cell's mechanism for protein synthesis to produce the protein encoded by the gene. An expression vector comprises expression elements including, for example, a promoter, the correct translation initiation sequence such as a ribosomal binding site and a start codon, a termination codon, and a transcription termination sequence. An expression vector may also comprise other regulatory regions such as enhancers, silencers and boundary elements/insulators to direct the level of transcription of a given gene. The expression vector can be a vector for stable or transient expression of a gene.

Anti-LSP1 Antibody

In a first aspect, the invention concerns an anti-LSP1 (Leukocyte specific protein 1) antibody comprising a variable domain that comprises three CDRs (complementarity determining regions), namely CDR1, CDR2 and CDR3, consisting or consisting essentially in the amino acid sequences of SEQ ID NO: 1, SEQ ID NO: 2 and SEQ ID NO: 3, or any antibody capable to compete with said anti-LSP1 antibody for the binding to LSP1. The anti-LSP1 antibody may comprise a variable domain that comprises one or several variant CDRs of said three CDRs, the variant CDR having no more than 1, 2 or 3 amino acid additions, deletions, substitutions, or combinations thereof in comparison with the sequences of SEQ ID NO: 1, SEQ ID NO: 2, and/or SEQ ID NO: 3.

Preferably the CDR1 consists or consists essentially in the amino acid sequence of SEQ ID NO: 1, the CDR2 consists or consists essentially in the amino acid sequence of SEQ ID NO: 2, and the CDR3 consists or consists essentially in the amino acid sequences of SEQ ID NO: 3.

In a particular embodiment the anti-LSP1 antibody consists in a variable domain as described above.

The anti-LSP1 antibody according to the invention can be any kind of antibody. In particular, the anti-LSP1 antibody can comprise, consist or consist essentially in a classical Y-shaped antibody with two heavy chains and light chains or a fragment thereof. Preferably said fragment comprises the antigen binding or variable region of the anti-LSP1 antibody. Said fragment may be selected, without limitation, from the group consisting in Fv, Fab, Fab', F(ab)$_2$, F(ab')$_2$, F(ab)$_3$, Fv, single-chain Fv (scFv), di-scFvs or sc(Fv)$_2$, dsFv, Fd, dAb, CDRs, VH, VL, minibodies, diabodies, and multi-specific antibodies formed from antibodies fragments.

The anti-LSP1 antibody according to the invention can also comprise, consist or consist essentially in a heavy-chain antibody. Preferably a heavy-chain antibody is selected from the heavy-chain antibodies from camelids or from cartilaginous fishes. More preferably, the anti-LSP1 antibody is a heavy-chain antibody derived from camelids. Camelids antibody encompasses in particular dromedary, camel, lama and alpaca. Preferably, the anti-LSP1 antibody is a heavy-chain antibody derived from lama.

In a preferred embodiment, the anti-LSP1 antibody comprises, consists, or consists essentially in a single domain antibody or a fragment thereof. The single domain antibody can derive from a VHH or a V-NAR, preferably from a VHH. In particular, the anti-LSP1 antibody according to the invention can be a humanized single domain antibody, in particular a humanized VHH, or a fragment thereof.

Preferably, said fragment of the single domain antibody comprises the three CDRs.

Preferably, said fragment of the single domain antibody is still able to bind LSP1.

Optionally, the anti-LSP1 antibody according to the invention is a single domain antibody fused to an Fc region, preferably an Fc region selected from the group consisting in IgA, IgD, IgE, IgG, and IgM Fc regions, more preferably an IgG Fc region.

Preferably, the Fc region is selected from human, mouse and rabbit Fc regions. Even more preferably, the anti-LSP1 antibody according to the invention is a single domain antibody fused to a human Fc region.

In a most preferred embodiment, the anti-LSP1 antibody according to the invention is a single domain antibody fused to a human IgG Fc region.

The anti-LSP1 antibody according to the invention may be a monomeric antibody or a multimeric antibody. In particular, the anti-LSP1 antibody according to the invention may be a monomeric antibody, preferably a single domain monomeric antibody.

The anti-LSP1 antibody according to the invention may also be a multimeric antibody. When the anti-LSP1 antibody is a multimeric classical Y-shape antibody, it is preferably a dimer or a pentamer. Preferably, the anti-LSP1 antibody is a multimeric single domain antibody, preferably a dimerized single domain antibody.

In a multimeric antibody, preferably a single domain antibody, the variable domains of the different monomers can be identical (i.e. homomeric) or different (i.e. heteromeric). Preferably, the multimeric antibody according to the invention is homomeric. When the multimeric antibody according to the invention is heteromeric, the variable domains of the different monomers can all bind the same protein, i.e. the LSP1 protein. Alternatively, one monomer can bind the LSP1 protein while another or some other monomers can bind other proteins, preferably a protein expressed at the membrane of the inflammatory dendritic cells.

In a particularly preferred embodiment, the anti-LSP1 antibody according to the invention is a single domain antibody, preferably a multimeric single domain antibody, more preferably a dimeric single domain antibody, still more preferably a homo-dimeric single domain antibody, even more preferably a homo-dimeric single domain antibody fused to an Fc region, preferably a human IgG Fc region.

In a particular embodiment, the different monomers of a multimeric single domain antibody are fused to different Fc regions.

The anti-LSP1 antibody according to the invention can be monoclonal or polyclonal. Preferably, the anti-LSP1 antibody according to the invention is monoclonal.

The anti-LSP1 antibody according to the invention comprises at least a variable domain. It may comprise several variable domains, in particular when the antibody is multimeric.

A variable domain of the anti-LSP1 antibody according to the invention comprises at least three CDRs. Preferably, the anti-LSP1 antibody according to the invention comprises three CDRs, namely CDR1, CDR2 and CDR3. The at least three CDRs according to the invention consist or consist essentially in the amino acid sequences of SEQ ID NO: 1, SEQ ID NO: 2 and SEQ ID NO: 3. In a particular embodiment, one, two or the three CDRs having the amino acid sequences of SEQ ID NO: 1, SEQ ID NO: 2 and SEQ ID NO: 3 may be replaced by variant CDRs having no more than 1, 2, 3, 4, 5, 6, preferably no more than 1, 2 or 3, amino acid modifications within the sequences of SEQ ID NO: 1, SEQ ID NO: 2, and/or SEQ ID NO: 3. In particular, the variant CDR can have 1 or 2 amino acid modifications. Thus, the three CDRs may be selected from the following list of combinations:

CDRs of sequences of SEQ ID NO: 1, SEQ ID NO: 2 and SEQ ID NO: 3;

CDRs of sequences of SEQ ID NO: 1, SEQ ID NO: 2 and a variant of SEQ ID NO: 3 having no more than 1, 2, 3, 4, 5, 6, preferably no more than 1, 2 or 3, amino acid modifications, still more preferably 1 or 2 modifications;

CDRs of sequences of SEQ ID NO: 1, a variant of SEQ ID NO: 2 having no more than 1, 2, or 3, preferably no more than 1 or 2 3, amino acid modifications, and SEQ ID NO: 3;

CDRs of sequences of a variant of SEQ ID NO: 1 having no more than 1, 2 or 3, preferably no more than 1 or 2, amino acid modifications, SEQ ID NO: 2, and SEQ ID NO: 3;

CDRs of sequences of a variant of SEQ ID NO: 1 having no more than 1, 2 or 3, preferably no more than 1 or 2, amino acid modifications, SEQ ID NO: 2 and a variant of SEQ ID NO: 3 having no more than 1, 2, 3, 4, 5, 6, preferably no more than 1, 2 or 3, amino acid modifications;

CDRs of sequences of SEQ ID NO: 1, a variant of SEQ ID NO: 2 having no more than 1, 2 or 3, preferably no more than 1 or 2, amino acid modifications, and a variant of SEQ ID NO: 3 having no more than 1, 2, 3, 4, 5, 6, preferably no more than 1, 2 or 3, amino acid modifications; or CDRs of sequences of a variant of SEQ ID NO: 1 having no more than 1, 2 or 3, preferably no more than 1 or 2, amino acid modifications, a variant of SEQ ID NO: 2 having no more than 1, 2 or 3, preferably no more than 1 or 2, amino acid modifications, and a variant of SEQ ID NO: 3 having no more than 1, 2, 3, 4, 5, 6, preferably no more than 1, 2 or 3, amino acid modifications.

The modifications of the CDRs may be selected from the group consisting in additions, deletions, substitutions, and combinations thereof. Preferably the modifications are substitutions. More preferably, the modifications are conservative substitutions.

In a preferred embodiment, a variable domain of the anti-LSP1 antibody according to the invention comprises the sequence FR1-CDR1-FR2-CDR2-FR3-CDR3-FR4, wherein FR1, FR2, FR3 and FR4 are framework regions and CDR1, CDR2 and CDR3 are complementary determining regions.

The variable domain of the anti-LSP1 antibody according to the invention may comprise CDR domains as follow:

CDR1 consists or consists essentially in an amino acid sequence of SEQ ID NO: 1 or any variant CDR of CDR1 with no more than 1, 2 or 3 amino acid additions, deletions, substitutions, or combinations thereof, preferably substitution, in comparison with the sequence of SEQ ID NO: 1;

CDR2 consists or consists essentially in an amino acid sequence of SEQ ID NO: 2 or any variant CDR of CDR2 with no more than 1, 2 or 3 amino acid additions, deletions, substitutions, or combinations thereof, preferably substitution, in comparison with the sequence of SEQ ID NO: 2; and/or CDR3 consists or consists essentially in an amino acid sequence of SEQ ID NO: 3, or any variant CDR of CDR3 with no more than 1, 2 or 3 amino acid additions, deletions, substitutions, or combinations thereof, preferably substitution, in comparison with the sequence of SEQ ID NO: 3.

The above mentioned amino acids substitutions are preferably conservative substitutions.

In a particular embodiment, the variable domain of an anti-LSP1 antibody according to the invention may comprise:

a CDR1 domain having an amino acid sequence consisting in the amino acid sequence of SEQ ID NO: 1 with no more than 1 amino acid addition, deletion, or substitution, preferably substitution, more preferably conservative substitution;

a CDR2 domain having an amino acid sequence consisting in the amino acid sequence of SEQ ID NO: 2 with no more than 1 amino acid addition, deletion, or substitution, preferably substitution, more preferably conservative substitution; and a CDR3 domain having an amino acid sequence consisting in the amino acid sequence of SEQ ID NO: 3 with no more than 1, 2 or 3 amino acid additions, deletions, or substitutions, preferably substitutions, more preferably conservative substitutions.

In another particular embodiment, the variable domain of an anti-LSP1 antibody according to the invention may comprise:

a CDR1 domain having an amino acid sequence consisting in the amino acid sequence of SEQ ID NO: 1 with no more than 2 amino acid additions, deletions, substitutions, or combination thereof, preferably substitutions, more preferably conservative substitutions;

a CDR2 domain having an amino acid sequence consisting in the amino acid sequence of SEQ ID NO: 2 with no more than 2 amino acid additions, deletions, substitutions, or combination thereof, preferably substitutions, more preferably conservative substitutions; and a CDR3 domain having an amino acid sequence consisting in the amino acid sequence of SEQ ID NO: 3 with no more than 2 or 3 amino acid additions, deletions, substitutions, or combination thereof, preferably substitutions, more preferably conservative substitutions.

In yet another particular embodiment, the variable domain of an anti-LSP1 antibody according to the invention may comprise:

a CDR1 domain having an amino acid sequence consisting in the amino acid sequence of SEQ ID NO: 1 with no more than 3 amino acid additions, deletions, substitutions, or combination thereof, preferably substitutions, more preferably conservative substitutions;

a CDR2 domain having an amino acid sequence consisting in the amino acid sequence of SEQ ID NO: 2 with no more than 3 amino acid additions, deletions, substitutions, or combination thereof, preferably substitutions, more preferably conservative substitutions; and a CDR3 domain having an amino acid sequence consisting in the amino acid sequence of SEQ ID NO: 3 with no more than 3 amino acid additions, deletions, substitutions, or combination thereof, preferably substitutions, more preferably conservative substitutions.

Preferably, the variable domain of an anti-LSP1 antibody according to the invention comprises a CDR1 domain consisting in the amino acid sequence of SEQ ID NO: 1, a CDR2 domain consisting in the amino acid sequence of SEQ ID NO: 2, and a CDR3 domain consisting in the amino acid sequence of SEQ ID NO: 3.

FR1, FR2, FR3 and FR4 of the variable domain of the invention may be naturally occurring VHH framework regions, i.e. framework regions from Camelidae, preferably from dromedary, camel, lama or alpaca, more preferably from lama. FR1, FR2, FR3 and FR4 may also be humanized framework regions of a VHH, preferably from Camelidae, more preferably from lama species, or camelized framework regions of a human VH.

As used herein a "humanized framework region of a VHH" refers to a framework region of a VHH wherein some amino acids are substituted with amino acids from a human VH framework region.

As used herein, a "camelized framework region of a human VH" refers to a framework region of a human VH wherein some amino acids are substituted with amino acids from a VHH framework region.

In a most preferred embodiment, the framework regions of a variable domain of the anti-LSP1 antibody according to the invention comprises camelid VHH amino acid residues and human VH amino acid residues.

The patent application WO2015/063331 provides direction for preparing synthetic single domain antibody.

Preferably, the framework regions comprise one of the following lists of amino acids residues, the positions of the amino acid residues are indicated according to the Kabat numbering nomenclature used for VH amino acid sequences:

P15 in FR1; F37, E44, R45, F47, and S49 in FR2; S81, R93, and A94 in FR3; or

Q8 and P15 in FR1; F37, E44, R45, F47, and S49 in FR2; S81, R93, A94, T99 in FR3; and Q108 in FR4; or F12 and P15 in FR1; S49 in FR2; S81, K82, V85, Y86, S91, R93 and A94 in FR3; or Q8, A9, F12, and P15 in FR1; F37, K43 E44, R45, F47, S49, and A50 in FR2; S81, K82, V85, Y86, S91, R93, A94, and T99 in FR3; and Q108 in FR4.

More preferably, the framework regions comprise Q8, A9, F12, and P15 in FR1; F37, K43 E44, R45, F47, S49, and A50 in FR2; S81, K82, V85, Y86, S91, R93, A94, and T99 in FR3; and Q108 in FR4.

These amino acid residues are present, for example, in SEQ ID NO: 8: Q7, A8, F13, P16, F39, K45, E46, R47, F49, S51, A52, S78, K79, V82, Y83, S88, R90, A91, T96, and Q119.

In a preferred embodiment, the variable domain of an anti-LSP1 antibody according to the invention comprises frameworks regions as follow:

FR1 consists or consists essentially in an amino acid sequence having at least 50%, 60%, 70%, 80%, 90%, 95%, sequence identity with the sequence of SEQ ID NO: 4, preferably FR1 has the amino acid sequence of SEQ ID NO: 4;

FR2 consists or consists essentially in an amino acid sequence having at least 50%, 60%, 70%, 80%, 90%, 95%, sequence identity with the sequence of SEQ ID NO: 5, preferably FR2 has the amino acid sequence of SEQ ID NO: 5;

FR3 consists or consists essentially in an amino acid sequence having at least 50%, 60%, 70%, 80%, 90%, 95%, sequence identity with the sequence of SEQ ID NO: 6, preferably FR3 has the amino acid sequence of SEQ ID NO: 6; and/or FR4 consists or consists essentially in an amino acid sequence having at least 50%, 60%, 70%, 80%, 90%, 95%, sequence identity with the sequence of SEQ ID NO: 7, preferably FR4 has the amino acid sequence of SEQ ID NO: 7.

In a particular embodiment, the variable domain of an anti-LSP1 antibody according to the invention may comprise a FR1 having an amino acid sequence having at least 70% sequence identity with the sequence of SEQ ID NO: 4, a FR2 having an amino acid sequence having at least 70% sequence identity with the sequence of SEQ ID NO: 5, a FR3 having an amino acid sequence having at least 70% sequence identity with the sequence of SEQ ID NO: 6, and a FR4 having an amino acid sequence having at least 70% sequence identity with the sequence of SEQ ID NO: 7.

In another particular embodiment, the variable domain of an anti-LSP1 antibody according to the invention may comprise a FR1 having an amino acid sequence having at least 80% sequence identity with the sequence of SEQ ID NO: 4, a FR2 having an amino acid sequence having at least 80% sequence identity with the sequence of SEQ ID NO: 5, a FR3 having an amino acid sequence having at least 80% sequence identity with the sequence of SEQ ID NO: 6, and a FR4 having an amino acid sequence having at least 80% sequence identity with the sequence of SEQ ID NO: 7.

In yet another particular embodiment, the variable domain of an anti-LSP1 antibody according to the invention may comprise a FR1 having an amino acid sequence having at least 90% sequence identity with the sequence of SEQ ID NO: 4, a FR2 having an amino acid sequence having at least 90% sequence identity with the sequence of SEQ ID NO: 5, a FR3 having an amino acid sequence having at least 90% sequence identity with the sequence of SEQ ID NO: 6, and a FR4 having an amino acid sequence having at least 90% sequence identity with the sequence of SEQ ID NO: 7.

In still another particular embodiment, the variable domain of an anti-LSP1 antibody according to the invention may comprise a FR1 having an amino acid sequence having at least 95% sequence identity with the sequence of SEQ ID NO: 4, a FR2 having an amino acid sequence having at least 95% sequence identity with the sequence of SEQ ID NO: 5, a FR3 having an amino acid sequence having at least 95% sequence identity with the sequence of SEQ ID NO: 6, and a FR4 having an amino acid sequence having at least 95% sequence identity with the sequence of SEQ ID NO: 7.

Preferably, the variable domain of an anti-LSP1 antibody according to the invention comprises a FR1 having the amino acid sequence of SEQ ID NO: 4, a FR2 having the amino acid sequence of SEQ ID NO: 5, a FR3 having the amino acid sequence of SEQ ID NO: 6, and a FR4 having the amino acid sequence of SEQ ID NO: 7.

In a particularly preferred embodiment, a variable domain of the anti-LSP1 antibody according to the invention comprises, consists in, or consists essentially in, the amino acid sequence of SEQ ID NO: 8 or a variant amino acid sequence having no more than 1, 2, 3, 4, 5, 6, 7, 8, 9, or 10, preferably no more than 1, 2, 3, 4, 5, 6, even more preferably no more than 1, 2, 3, amino acid additions, deletions, substitutions, or combinations thereof, preferably substitutions, more preferably conservative substitutions, within the sequence of SEQ ID NO: 8.

Preferably, said additions, deletions, substitutions, or combinations thereof are present in the framework regions of said variable domains, i.e. in the amino acids segments 1-28, 36-54, 62-100 and 113-124.

In a most preferred embodiment, a variable domain of the anti-LSP1 antibody according to the invention, preferably a single domain antibody, consists in the amino acid sequence of SEQ ID NO: 8.

The anti-LSP1 antibody according to the invention can be any antibody as described above or any protein, preferably an antibody, capable to compete with said anti-LSP1 antibody for the binding to LSP1. In a particular aspect, the antibody is capable to compete with the anti-LSP1 antibody having the amino acid sequence of SEQ ID No: 8 for the binding to LSP1.

When an antibody is said to "compete with" a particular monoclonal antibody (e.g. anti-LSP1 antibody having the amino acid sequence of SEQ ID No: 8 (D4)), it means that the antibody competes with the antibody in a binding assay using either recombinant LSP1 molecules or surface expressed LSP1 molecules. For example, if a test antibody reduces the binding of D4 antibody to a LSP1 polypeptide or LSP1-expressing cell in a binding assay, the antibody is said to "compete" respectively with D4.

The competition assay can be carried out with purified LSP1 or with a cell expressing LSP1. The cell can express LSP1 intracellularly and the cell is permeabilized for carrying out the assay. Preferably, the cell expressing LSP1 is an inflammatory dendritic cell.

Labeled Antibody and Detection Entity Fused Antibody

The anti-LSP1 antibody according to the invention can be labelled and/or fused to a detection entity. Preferably, the anti-LSP1 antibody according to the invention is labelled or fused to a detection entity.

In a preferred embodiment, the anti-LSP1 antibody is labelled. The anti-LSP1 antibody can be labelled with a label selected from the group consisting in a radiolabel, an enzyme label, a fluorescent label, a biotin-avidin label, a chemiluminescent label, and the like. The anti-LSP1 antibody according to the invention can be labeled by standard labeling techniques well known by the man skilled in the art and labelled antibodies can be visualized using known methods. In particular, labels generally provide signals detectable by fluorescence, chemiluminescence, radioactivity, colorimetry, mass spectrometry, X-ray diffraction or absorption, magnetism, enzymatic activity, or the like.

Preferably, the detectable label may be a luminescent label. For example, fluorescent labels, bioluminescent labels, chemiluminescent labels, and colorimetric labels may be used in the practice of the invention, more preferably a fluorescent label.

The terms "fluorescent label", "fluorophore", "fluorogenic dye", "fluorescent dye" as used herein are interchangeable and designate a functional group attached to the anti-LSP1 antibody of the invention that will absorb energy at a specific wavelength and re-emit energy at a different, but equally specific, wavelength.

Fluorescent labels that can be used in the context of this invention include, but are not limited to, fluorescein, a phosphor, a rhodamine, or a polymethine dye derivative. Additionally, commercially available fluorescent labels including, but not limited to, fluorescent phosphoramidites such as FluorePrime, Fluoredite, FAM, hydroxycoumarin, aminocoumarin, methoxycoumarin, cascade Blue, pacific Blue, pacific Orange, lucifer yellow, R-phycoerythrin, PE-Cy5 conjugates, PE-Cy7 conjugates, red 613, perCP, truRed, fluorX, fluorescein, BODIPY-FL, Cy2, Cy3, Cy3B, Cy3.5, Cy5, Cy5.5, Cy7, TRITC, X-Rhodamine, lissamine Rhodamine B, Texas Red, allophycocyanin (APC), APC-Cy7 conjugates can be used. The fluorescent label can be made of a combination of fluorescent labels listed above.

Preferably, the label is linked at the C-terminal extremity of the anti-LSP1 antibody.

In another preferred embodiment, the above mentioned anti-LSP1 antibody can be fused to a detection entity. The detection entity may be selected from the group consisting of a tag, an enzyme or a fluorescent protein.

Preferably, the detection entity is at the C-terminal extremity of the anti-LSP1 antibody.

The anti-LSP1 antibody can be fused to a tag. As used herein, the term "tag" refers to a protein or peptide sequence genetically grafted onto a recombinant protein and that can be detected by specific antibodies. Appropriate tags encompass, without being limited to, FLAG-Tag, His-tag, Strep-tag, Avi-tag, HA-tag (hemagglutinin-tag), S-tag, E-tag, V5-tag, Xpress-tag, VSV-tag, SBP-tag, Softag 1, Softag 2, Softag 3, Isopetag, Spy-tag calmodulin-tag, Myc-tag, ProtA-tag (proteine A from *Staphylococcus aureus*), Polyglutamate-tag, Tetracysteine-tag, Thioredoxin-tag, NusA-tag, GST-tag (Glutathion-S-Transferase-tag), CBP-tag (Chitin Binding Protein-tag), MBP-tagt (Maltose Binding Protein-tag), and the like. Preferably, the tag is a FLAG-tag.

The anti-LSP1 antibody can also be fused to an enzyme. Appropriate enzymes encompass, without being limited to, horseradish peroxidase, or luciferase. Horseradish peroxidase is an enzyme that catalyzes the conversion of chromogenic substrates (e.g., TMB, DAB, ABTS) into colored products, and that even produces light when acting on chemiluminescent substrates (e.g. Enhanced Chemiluminescence by luminol). Luciferase is a generic term for the class of oxidative enzymes that produce bioluminescence, for example the firefly luciferase (EC 1.13.12.7) from the firefly *Photinus pyralis*.

The anti-LSP1 antibody can also be fused to a fluorescent protein. As used herein "fluorescent protein" refers to proteins that are members of a structurally homologous class of proteins that share the unique property of being self-sufficient to form a visible wavelength chromophore from a sequence of 3 amino acids within their own polypeptide sequence. Fluorescent proteins can be genetically grafted onto a recombinant protein allowing to subsequently visualize the location of the protein using fluorescence microscopy. Appropriate fluorescent proteins encompass, without being limited to, GFP (Green Fluorescent Protein), EGFP (Enhanced GFP), RFP (Red Fluorescent Protein), YFP (Yellow Fluorescent Protein), EYFP (Enhanced YFP), CFP (Cyan Fluorescent Protein), ECFP (Enhanced CFP), BFP (Blue Fluorescent Protein), Tag-BFP, T-Sapphire, mPlum, AQ143, mCherry, tdTomato, mStrawberry, J-Red, DsRed-Monomer, mOrange, mOrange2, mKO, mKO2, mCitrine, Venus, YPet, Emerald, Cerulean, CyPet, mTagBFP, mTurquoise, mApple, mKate2, Sirius, Azurite, mTFP1, mUKG1, mAG1, AcGFP1, TagGFP2, mWasabi, EmGFP, TagYFP, Topaz, SYFP2, TagRFP, TagRFP-T, mRuby, mRasperry, mPlum, mNeptune, mAmetrine, mKeima, Sirius, mBlueberry, mHoneydew, AmCyan1, Midori-Ishi Cyan, copGFP, TurboGFP, ZsGreen, TurboYFP, Zs Yellow1, TurboRFP, DsRed2, DsRed-express, DsRed-Express2, DsRed-Max, AsRed2, TurboFP602, RFP611, Katushka, Katushka2, AQ143, PA-GFP, anm2CP (KillerRed), Dronpa, KikG, EosFP, Kaede (red), Kaede (green), dendGFP, EBFP2, mKalama1, Sapphire, SCFP3A, mTurquoise2, monomeric Midoriishi-Cyan, TagCFP, Superfolder GFP, Monomeric Azami Green, mUKG, Clover, mNeonGreen, Citrine, Monomeric Kusabira-Orange, mKOk, mTangerine, mRuby2, HcRed-Tandem, NirFP, TagRFP657, TagBFP, mTagBFP2, IFP1.4, iRFP, mKeima Red, LSS-mKate1, LSS-mKate2, mBeRFP, PA-GFP, PAmCheryl, PATagRFP, KikGR1 (green), KikGR1 (red), PS-CFP2, mEos2(green), mEos2 (red), mEos3.2 (green), mEos3.2 (red), PSmOrange, and Dronpa cFP484.

Production of the Anti-LSP1 Antibody

In a second aspect, the invention also concerns an isolated nucleic acid comprising a sequence encoding an anti-LSP1 antibody according to the invention, preferably a single-domain antibody.

The invention also relates to an expression cassette comprising a nucleic acid according to the invention and a promoter.

The invention then relates to a vector, preferably an expression vector, comprising a nucleic acid or an expression cassette according to the invention. Preferably, the vector is such that a nucleic acid sequence encoding said anti-LSP1 antibody is operably linked to a promoter and optionally to other regulatory elements such as e.g. terminators, enhancers, polyadenylation signals, signal sequences for secretion, and the like. Such vectors are particularly useful for the recombinant production of the anti-LSP1 antibody according to the invention. For instance, the vector is transfected in an appropriate host cell and the host cell is then cultured in conditions allowing the production of the anti-LSP1 antibody according to the invention. For review about the recombinant expression of a given protein, one may refer for instance to Ausubel et al, "*Current Protocols in Molecular Biology*", Greene Publishing and Wiley-Interscience, New York (1987) and in Sambrook and Russell (2001) "*Molecular Cloning: A Laboratory Manual (3(rd) edition), Cold Spring Harbor Laboratory*, Cold Spring Harbor Laboratory Press, New York).

The invention also pertains to a host cell comprising a nucleic acid, an expression cassette, or a vector according to the invention. The host cell may be used for the production of an anti-LSP1 antibody according to the invention. The host cell may be any host cell capable of producing said anti-LSP1 antibody, including e.g. a prokaryotic host cell, such as e.g., *E. coli*, or a (cultured) mammalian, plant, insect, fungal or yeast host cell, including e.g. CHO-cells, BHK-cells, human cell lines (including HeLa, COS and PER C6), Sf9 cells and Sf+ cells. An appropriate host cell encompasses a cell of an eukaryotic microorganism such as yeasts and filamentous fungi. Preferred yeast host cell include *Saccharomyces cerevisiae, Pichia pastoris, Hansenula polymorpha,* and *Kluyveromyces lactis*. For illustration of appropriate strains, constructs and fermentation conditions for production of the anti-LSP1 antibody according to the invention, see, for instance, van de Laar et al., (*Biotechnology and Bioengineering,* 2007, 96, 3:483-494).

A further object of the invention is a method for producing anti-LSP1 antibody according to the invention, wherein the method comprises the steps of:
a) culturing a host cell as previously-defined and
b) recovering the said anti-LSP1 antibody from the cell culture.

It goes without saying that step a) is performed under conditions allowing the expression of the desired anti-LSP1 antibody by the host cell. Suitable expression conditions may include the use of a suitable medium, the presence of a suitable source of food and/or suitable nutrients, a suitable temperature, and optionally the presence of a suitable inducing factor or compound (e.g. when the nucleotide sequences of the invention are under the control of an inducible promoter); all of which may be selected by the skilled artisan.

Under such conditions, the anti-LSP1 antibody of the invention may be expressed in a constitutive manner, in a transient manner, or only when suitably induced. The anti-LSP1 antibody may be produced, for instance, as inclusion bodies or secreted in the culture medium.

The anti-LSP1 antibody of the invention may then be isolated from the host cell and/or from the culture medium in which said host cell was cultivated, using protein isolation and/or purification techniques known per se, such as chromatography and/or electrophoresis techniques, differential precipitation techniques, affinity techniques and the like.

As an alternative, the anti-LSP1 antibody of the invention may be produced by a transgenic mammal such as of transgenic rabbits, goats, or sheep. For instance, they may be recovered from the milk of said transgenic animal. Another option is the production of the anti-LSP1 antibody of the invention in a transgenic plant, such as a transgenic tobacco.

Use of an Anti-LSP1 Antibody as a Research Tool

In a third aspect, the invention also relates to the use of an anti-LSP1 antibody according to the invention as a research tool. Indeed, the anti-LSP1 antibody is useful for specific binding, e.g. to LSP1 protein and more particularly to LSP1 protein expressed at cell surface (in particular on inflammatory DC), for purification of proteins or cells, e.g. to LSP1 protein and more particularly to LSP1 protein expressed at cell surface (in particular on inflammatory DC), for the immuno-staining of cells (in particular specific of inflammatory DC), or for in-vivo imaging of inflammatory dendritic cells, identification of cells by flow cytometry.

For instance, the anti-LSP1 antibody according to the invention, preferably a labelled anti-LSP1 antibody or an anti-LSP1 antibody fused to a detection entity, may be used for in-vitro or in-vivo imaging of inflammatory dendritic cells. The anti-LSP1 antibody may also be used for inflammatory dendritic cells sorting, for example by FACS, and purification.

The anti-LSP1 antibody of the invention may also be used in cell immune-staining, such as Western-blot, ELISA, RIA, EIA and other "sandwich assays" immunoassays.

The Anti-LSP1 Antibody as a Diagnosis Marker

In a fourth aspect, the invention also concerns the use of an anti-LSP1 antibody according to the invention as a diagnosis marker, in particular for inflammatory pathologies.

Preferably, inflammatory pathologies according to the invention are selected from the group consisting in chronic inflammatory pathologies, autoimmune diseases, autoinflammatory diseases, allergies and cancers.

Preferably, the inflammatory pathology of the invention is an inflammatory pathology involving Th17.

In a preferred embodiment, the inflammatory pathology is selected from the group consisting in rheumatoid arthritis, juvenile idiopathic arthritis, asthma, inflammatory bowel diseases such as Crohn's disease and ulcerative colitis, tumor ascites, psoriasis, acne vulgaris, atopic dermatitis, chronic non-healing skin ulcers, photoaging (skin aging), systemic lupus erythematosus, granuloma, chronic gastritis, chronic prostatitis, diverticulitis, interstitial cystitis, glomerulonephritis, celiac disease, chronic obstructive pulmonary disease, pelvic inflammatory disease, vasculitis, periodontitis, advanced atherosclerosis, encephalomyelitis, Sjögren syndrome, multiple sclerosis, myasthenia gravis, systemic sclerosis, primary sclerosing cholangitis, ankylosing spondylitis, rheumatic fever, aneurysm (abdominal, thoracic, cerebral), sarcoidosis, hidradenitis suppurativa, hypersensitivities, type 1 diabetes, autoimmune thyroid disorders such as Graves' disease and Hashimoto's disease, reperfusion injury, and transplant rejection, even more preferably the inflammatory pathology is selected from the group consisting in rheumatoid arthritis, juvenile idiopathic arthritis, asthma, inflammatory bowel diseases such as Crohn's disease and ulcerative colitis, tumor ascites, and psoriasis.

The invention also concerns a method for diagnosis of inflammatory pathologies in a subject wherein the method comprises a step of staining inflammatory dendritic cells in a sample with an anti-LSP1 antibody according to the invention.

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, that are in need of diagnostic. Preferably, the human subject according to the invention is an adult, more preferably an adult of at least 40 years old, still more preferably an adult of at least 50 years old, even more preferably an adult of at least 60 years old.

The method may be in vivo or in-vitro.

When the method is an in-vivo method, the anti-LSP1 antibody, preferably a labelled anti-LSP1 antibody or an anti-LSP1 antibody fused to a detection entity, is administered to the patient, preferably via a parenteral route of administration, in particular via a blood injection or a direct injection into the organ or tissue suspected to be under inflammation.

Preferably, the method is an in-vitro method comprising a step of staining inflammatory dendritic cells in a biological sample from said subject.

Prior to this step, the method may further comprise a step of obtaining or providing a sample from the subject.

The term "biological sample", as used herein, refers to any sample containing inflammatory dendritic cells derived from the subject. Examples of such a biological sample include biopsies, organs, tissues or cell samples. Preferably, the biological sample is a biopsy sample.

In a preferred embodiment, the method for diagnosing inflammatory pathologies in a subject further comprises a step of determining the quantity of inflammatory dendritic cells in a biological sample. The quantity of inflammatory dendritic cells may be measured by semi-quantitative Western blots, enzyme-labeled and mediated immunoassays, such as ELISAs, biotin/avidin type assays, radioimmunoassay, immunoelectrophoresis or immunoprecipitation or by protein or antibody arrays. The quantity of inflammatory dendritic cells in a biological sample may also be assessed by immunohistochemistry on a section of the biological sample (e.g. frozen or formalin-fixed paraffin embedded material). The reactions generally include revealing labels linked to the anti-LSP1 antibody or detecting entity fused to the anti-LSP1 antibody, or other methods for detecting the formation of a complex between the antigen and the anti-LSP1 antibody.

In a yet preferred embodiment, the method for diagnosis of inflammatory pathologies in a subject further comprises a step of determining the proportion of inflammatory dendritic cells in relation to total dendritic cells, a proportion of at least 10%, preferably 5%, more preferably 1%, still more preferably 0.5%, even more preferably 0.1%, being indicative of an inflammatory pathology. Preferably, the simple presence of inflammatory dendritic cells (i.e. non null proportion) is already indicative of an inflammatory pathology.

Quantity of total dendritic cells in a biological sample may be assess through a double staining with an anti-CD11c antibody (which is an antibody specific of monocytes, macrophages and dendritic cells) and a BDCA-1/CD1c antibody (which is an antibody specific of B Lymphocytes and dendritic cells).

In a particular embodiment, the method further comprises a step of selecting a subject having a proportion of inflammatory dendritic cells in relation to total dendritic cells of at least 10%, preferably 5%, more preferably 1%, still more preferably 0.5%, even more preferably 0.1%, for a treatment with an anti-inflammatory drug. Alternatively, patients who present inflammatory dendritic cells in their biological sample are selected for a treatment with an anti-inflammatory drug.

The method may also further comprise a step of administering an anti-inflammatory drug to subjects having a proportion of inflammatory dendritic cells in relation to total dendritic cells of at least 10%, preferably 5%, more preferably 1%, still more preferably 0.5%, even more preferably 0.1%, or to subjects having inflammatory dendritic cells in their biological sample.

The anti-inflammatory drug according to the invention can be selected from the group consisting in salicylates such as aspirin (acetylsalicylic acid), diflunisal (dolobid), and salsalate (disalcid); propionic acid derivatives such as ibuprofen, dexibuprofen, naproxen, fenoprofen, ketoprofen, dexketoprofen, flurbiprofen, oxaprozin, and loxoprofen; acetic acid derivatives such as indomethacin, tolmetin, sulindac, etodolac, ketorolac, diclofenac, aceclofenac, and nabumetone; enolic acid (oxicam) derivatives such as piroxicam, meloxicam, tenoxicam, droxicam, lornoxicam, isoxicam, and phenylbutazone (bute); anthranilic acid derivatives (fenamates) such as mefenamic acid, meclofenamic acid, flufenamic acid, and tolfenamic acid; selective COX-2 inhibitors (coxibs), such as celecoxib, rofecoxib, valdecoxib, parecoxib, lumiracoxib, etoricoxib, and firocoxib; sulfonanilides such as nimesulide; immune selective anti-inflammatory derivatives such as phenylalanine-glutamine-glycine (FEG) and its d-isomeric form (feG); molecules targeting the TH17 pathway such as ustekinumab, briakinumab, olokizumab, sirukumab, tocilizumab, sarilumab, anakinra, ixekizumab, secukinumab, and brodalumab; tolmetin (tolectin), clonixin, licofelone, h-harpagide, plumbagin, plumericin, derivatives and combinations thereof.

Preferably, the anti-inflammatory drug is a molecule targeting the TH17 pathway, even more preferably selected from the group consisting in ustekinumab, briakinumab, olokizumab, sirukumab, tocilizumab, sarilumab, anakinra, ixekizumab, secukinumab, brodalumab, derivatives and combinations thereof.

The invention also concerns the use of an anti-LSP1 antibody according to the invention for selecting a subject for a treatment with an anti-inflammatory drug, or for predicting the efficacy of a treatment with an anti-inflammatory drug in a subject.

The invention also concern the use of the proportion of cells stained by an anti-LSP1 antibody in relation to total dendritic cells for selecting a subject for a treatment with an anti-inflammatory drug, or for predicting the efficacy of a treatment with an anti-inflammatory drug in said subject.

The invention also concerns an in vitro method for selecting a subject for a treatment with an anti-inflammatory therapy or for predicting the efficacy of a treatment with an anti-inflammatory drug in a subject, wherein the method comprises:
(a) measuring the quantity of cells stained by an anti-LSP1 antibody according to the invention in a biological sample from said subject,
(b) measuring the quantity of total dendritic cells in same sample,
(c) determining the proportion of inflammatory dendritic cells versus total dendritic cells in said sample,
(d) selecting subjects with a proportion of cells stained in their biological sample higher than at least 10%, preferably 5%, more preferably 1%, still more preferably 0.5%, even more preferably 0.1%, for a treatment with an anti-inflammatory drug.

An Anti-LSP1 Antibody Conjugated to a Drug or to an Antigen

In a particular embodiment, the invention relates to an anti-LSP1 antibody according to the invention conjugated to a molecule, preferably a drug or an antigen.

Preferably, the anti-LSP1 antibody according to the invention is conjugated to a drug. The drug conjugated to the anti-LSP1 antibody according to the invention can be a cytotoxic drug, an anti-inflammatory drug, or a combination thereof.

In particular, the drug conjugated to the anti-LSP1 antibody according to the invention can be an anti-inflammatory drug. The anti-inflammatory drug according to the invention can be selected from the list consisting in salicylates such as aspirin (acetylsalicylic acid), diflunisal (dolobid), and salsalate (disalcid); propionic acid derivatives such as ibuprofen, dexibuprofen, naproxen, fenoprofen, ketoprofen, dexketoprofen, flurbiprofen, oxaprozin, and loxoprofen; acetic acid derivatives such as indomethacin, tolmetin, sulindac, etodolac, ketorolac, diclofenac, aceclofenac, and nabumetone; enolic acid (oxicam) derivatives such as piroxicam, meloxicam, tenoxicam, droxicam, lornoxicam, isoxicam, and phenylbutazone (bute); anthranilic acid derivatives (fenamates) such as mefenamic acid, meclofenamic acid, flufenamic acid, and tolfenamic acid; selective COX-2 inhibitors (coxibs), such as celecoxib, rofecoxib, valdecoxib, parecoxib, lumiracoxib, etoricoxib, and firocoxib; sulfonanilides such as nimesulide; immune selective anti-inflammatory derivatives such as phenylalanine-glutamine-glycine (FEG) and its d-isomeric form (feG); molecules targeting the TH17 pathway such as ustekinumab, briakinumab, olokizumab, sirukumab, tocilizumab, sarilumab, anakinra, ixekizumab, secukinumab, and brodalumab; tolmetin (tolectin), clonixin, licofelone, h-harpagide, plumbagin, plumericin, derivatives and combinations thereof. Preferably, the anti-inflammatory therapy is a molecule targeting the TH17 pathway, even more preferably selected from the group consisting in ustekinumab, briakinumab, olokizumab, sirukumab, tocilizumab, sarilumab, anakinra, ixekizumab, secukinumab, brodalumab, derivatives and combinations thereof.

Preferably, the drug conjugated to an anti-LSP1 antibody according to the invention is a cytotoxic drug. As used herein, the term "cytotoxic drug" refers to a molecule that when entering in contact with a cell, eventually upon internalization into the cell, alters a cell function (e.g. cell growth and/or proliferation and/or differentiation and/or metabolism such as protein and/or DNA synthesis) in a detrimental way or leads to cell death. As used herein, the term "cytotoxic drug" encompasses toxins, in particular cytotoxins.

The cytotoxic drug according to the invention may be selected from the group consisting in abraxane, actinomycin, aldesleukin, alemtuzumab, altretamine, alitretinoin, amsacrine, anastrozole, arsenic, asparaginase, azacitidine, azathioprine, bcg, bexarotene, bendamustine, bicalutamide, bleomycin, bortezomib, busulfan, capecitabine, carboplatin, carmustine, cetuximab, chlorambucil, cisplatin, cladribine, clofarabine, cyclophosphamide, cytarabine, chloramphenicol, ciclosporin, cidofovir, coal tar containing products, colchicine, dacarbazine, dactinomycin, daunorubicin, danazol, dasatinib, diethylstilbestrol, dinoprostone, dithranol, dutasteride, dexrazoxane, docetaxel, doxifluridine, doxorubicin, epirubicin, erlotinib, estramustine, etoposide, exemestane, finasteride, flutamide, floxuridine, flucytosine, fludarabine, fluorouracil, ganciclovir, gefitinib, gemcitabine, gemtuzumab, goserelin, hydroxyurea, hydroxycarbamide, idarubicin, ifosfamide, irinotecan, imatinib, lenalidomide, leflunomide, letrozole, leuprorelin acetate, lomustine, mechlorethamine, melphalan, mercaptopurine, methotrexate, mitomycin, mitoxantrone, mitotane, menotropins, mifepristone, nafarelin, nelarabin, nitrogen mustard, nitrosoureas, oxaliplatin, ozogamicin, paclitaxel, podophyllyn, pegasparginase, pemetrexed, pentamidine, pentostatin, procarbazin, raloxifene, ribavarin, raltitrexed, rituximab, romidepsin, sorafenib, streptozocin, sunitinib, sirolimus, streptozocin, temozolomide, temsirolimus, teniposide, thalidomide, thioguanine, thiotepa, topotecan, tacrolimus, taxotere, tafluposide, toremifene, trastuzumab, tretinoin, trifluridine, triptorelin, valganciclovir, valrubicin, vinblastine, vidaradine, vincristine, vindesine, vinorelbine, vemurafenib, vismodegib, vorinostat, zidovudine, derivatives and combinations thereof.

Alternatively, the anti-LSP1 antibody according to the invention is conjugated to an antigen, preferably a cancer antigen.

In a preferred embodiment, the antibody-drug or antibody-antigen conjugates of the invention comprises a linker between the antibody and the drug or the antigen. The linker according to the invention may be cleavable or non-cleavable, preferably, the linker is cleavable. Examples of cleavable linkers according to the invention include, without limitations, disulfides, hydrazones and peptides. Examples of non-cleavable linkers according to the invention include, without limitations, thioethers.

In a particular embodiment, the drug or antigen is linked to a cysteine or a lysine residue of the antibody. Preferably, the drug or antigen is linked to an unnatural amino acids that has been incorporated into the antibody.

Methods to make antibody-drug or antibody-antigen conjugates are well known from the man skilled in the art.

Use of an Anti-LSP1 Antibody as a Drug

In another aspect, the invention concerns an anti-LSP1 antibody, preferably an anti-LSP1 antibody conjugated to a drug or to an antigen, for use as a drug.

The invention also concerns a pharmaceutical composition comprising an anti-LSP1 antibody, preferably an anti-LSP1 antibody conjugated to a drug or to an antigen, even more preferably an anti-LSP1 antibody conjugated to a drug, and at least one pharmaceutically acceptable excipient. For this formulation, conventional excipient can be used according to techniques well known by those skilled in the art.

In a preferred embodiment, the invention concerns an anti-LSP1 antibody conjugated to a drug, preferably an anti-inflammatory drug and/or a cytotoxic drug, more preferably a cytotoxic drug, or a pharmaceutical composition according to the invention, for use in the treatment of inflammatory pathologies.

The anti-inflammatory drug according to the invention can be selected from the list consisting in salicylates such as aspirin (acetylsalicylic acid), diflunisal (dolobid), and salsalate (disalcid); propionic acid derivatives such as ibuprofen, dexibuprofen, naproxen, fenoprofen, ketoprofen, dexketoprofen, flurbiprofen, oxaprozin, and loxoprofen; acetic acid derivatives such as indomethacin, tolmetin, sulindac, etodolac, ketorolac, diclofenac, aceclofenac, and nabumetone; enolic acid (oxicam) derivatives such as piroxicam, meloxicam, tenoxicam, droxicam, lornoxicam, isoxicam, and phenylbutazone (bute); anthranilic acid derivatives (fenamates) such as mefenamic acid, meclofenamic acid, flufenamic acid, and tolfenamic acid; selective COX-2 inhibitors (coxibs), such as celecoxib, rofecoxib, valdecoxib, parecoxib, lumiracoxib, etoricoxib, and firocoxib; sulfonanilides such as nimesulide; immune selective anti-inflammatory derivatives such as phenylalanine-glutamine-glycine (FEG) and its d-isomeric form (feG); molecules targeting the TH17 pathway such as ustekinumab, briakinumab, olokizumab, sirukumab, tocilizumab, sarilumab, anakinra, ixekizumab, secukinumab, and brodalumab; tolmetin (tolectin), clonixin, licofelone, h-harpagide, plumbagin, plumericin, derivatives and combinations thereof. Preferably, the anti-inflammatory therapy is a molecule targeting the TH17 pathway, even more preferably selected from the group consisting in ustekinumab, briakinumab, olokizumab, sirukumab, tocilizumab, sarilumab, anakinra, ixekizumab, secukinumab, brodalumab, derivatives and combinations thereof.

The cytotoxic drug according to the invention may be selected from the group consisting in abraxane, actinomycin, aldesleukin, alemtuzumab, altretamine, alitretinoin, amsacrine, anastrozole, arsenic, asparaginase, azacitidine, azathioprine, bcg, bexarotene, bendamustine, bicalutamide, bleomycin, bortezomib, busulfan, capecitabine, carboplatin, carmustine, cetuximab, chlorambucil, cisplatin, cladribine, clofarabine, cyclophosphamide, cytarabine, chloramphenicol, ciclosporin, cidofovir, coal tar containing products, colchicine, dacarbazine, dactinomycin, daunorubicin, danazol, dasatinib, diethylstilbestrol, dinoprostone, dithranol, dutasteride, dexrazoxane, docetaxel, doxifluridine, doxorubicin, epirubicin, erlotinib, estramustine, etoposide, exemestane, finasteride, flutamide, floxuridine, flucytosine, fludarabine, fluorouracil, ganciclovir, gefitinib, gemcitabine, gemtuzumab, goserelin, hydroxyurea, hydroxycarbamide, idarubicin, ifosfamide, irinotecan, imatinib, lenalidomide, leflunomide, letrozole, leuprorelin acetate, lomustine, mechlorethamine, melphalan, mercaptopurine, methotrexate, mitomycin, mitoxantrone, mitotane, menotropins, mifepristone, nafarelin, nelarabin, nitrogen mustard, nitrosoureas, oxaliplatin, ozogamicin, paclitaxel, podophyllyn, pegasparaginase, pemetrexed, pentamidine, pentostatin, procarbazin, raloxifene, ribavarin, raltitrexed, rituximab, romidepsin, sorafenib, streptozocin, sunitinib, sirolimus, streptozocin, temozolomide, temsirolimus, teniposide, thalidomide, thioguanine, thiotepa, topotecan, tacrolimus, taxotere, tafluposide, toremifene, trastuzumab, tretinoin, trifluridine, triptorelin, valganciclovir, valrubicin, vinblastine, vidaradine, vincristine, vindesine, vinorelbine, vemurafenib, vismodegib, vorinostat, zidovudine, derivatives and combinations thereof.

The subject according to the invention is an animal, preferably a mammal, even more preferably a human. The subject may be a non-human animal, in particular selected from mammals such as dogs, cats, horses, cows, pigs, sheep and non-human primates, among others. Preferably, the subject is human, preferably an adult, more preferably an adult of at least 40 years old, still more preferably an adult of at least 50 years old, even more preferably an adult of at least 60 years old.

The inflammatory pathologies according to the invention are preferably selected from the group consisting in chronic inflammatory pathologies, autoimmune diseases, autoinflammatory diseases, allergies and cancers. Preferably, the inflammatory pathology of the invention is an inflammatory pathology involving Th17. In a preferred embodiment, the inflammatory pathology is selected from the group consisting in rheumatoid arthritis, juvenile idiopathic arthritis, asthma, inflammatory bowel diseases such as Crohn's disease and ulcerative colitis, tumor ascites, psoriasis, acne vulgaris, atopic dermatitis, chronic non-healing skin ulcers, photoaging (skin aging), systemic lupus erythematosus, granuloma, chronic gastritis, chronic prostatitis, diverticulitis, interstitial cystitis, glomerulonephritis, celiac disease, chronic obstructive pulmonary disease, pelvic inflammatory disease, vasculitis, periodontitis, advanced atherosclerosis, encephalomyelitis, Sjögren syndrome, multiple sclerosis, myasthenia gravis, systemic sclerosis, primary sclerosing cholangitis, ankylosing spondylitis, rheumatic fever, aneurysm (abdominal, thoracic, cerebral), sarcoidosis, hidradenitis suppurativa, hypersensitivities, type 1 diabetes, autoimmune thyroid disorders such as Graves' disease and Hashimoto's disease, reperfusion injury, and transplant rejection, even more preferably the inflammatory pathology is selected from the group consisting in rheumatoid arthritis, juvenile idiopathic arthritis, asthma, inflammatory bowel diseases such as Crohn's disease and ulcerative colitis, tumor ascites, and psoriasis.

The anti-LSP1 antibody conjugated to a drug or the pharmaceutical composition according to the invention may be administered by any convenient route. For instance, it can be administered by a systemic route, in particular by subcutaneous, intramuscular, intravenous or intradermal, preferably by intravenous, injection. It can also be directly administered in the inflammatory organ or tissue.

The anti-LSP1 antibody conjugated to a drug or the pharmaceutical composition according to the invention may be administered as a single dose or in multiple doses.

The anti-LSP1 antibody conjugated to a drug or the pharmaceutical composition according to the invention may be administered between every day and every month, preferably every week or every two weeks, more preferably every week.

The duration of treatment with an anti-LSP1 antibody conjugated to a drug, or with a pharmaceutical composition according to the invention, is preferably comprised between 1 and 20 weeks, preferably between 1 and 10 weeks. Alternatively, the treatment may last as long as the inflammation persists.

The amount of anti-LSP1 antibody conjugated to a drug or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

The invention also relates to the use of an anti-LSP1 antibody conjugated to a drug or a pharmaceutical composition according to the invention, for the preparation of a medicament. Preferably, it relates to an anti-LSP1 antibody conjugated to an anti-inflammatory drug and/or a cytotoxic drug, preferably a cytotoxic drug, or a pharmaceutical composition according to the invention, for the preparation of a medicament for treating inflammatory pathologies in a subject.

It further relates to a method for treating in a subject an inflammatory pathology, wherein a therapeutically effective amount of an anti-LSP1 antibody conjugated to a drug, preferably an anti-inflammatory drug and/or a cytotoxic drug, or a therapeutically effective amount of a pharmaceutical composition according to the invention, is administered to said subject suffering from an inflammatory pathology.

The invention also concerns an anti-LSP1 antibody conjugated to an antigen, preferably a cancer antigen, for use in the treatment of cancer.

It also relates to a pharmaceutical composition comprising an anti-LSP1 antibody conjugated to an antigen, preferably a cancer antigen, and at least one pharmaceutically acceptable excipient.

It yet relates to the use of an anti-LSP1 antibody conjugated to an antigen, preferably a cancer antigen, or a pharmaceutical composition according to the invention, for the preparation of a medicament. Preferably, it relates to an anti-LSP1 antibody conjugated to an antigen, preferably a cancer antigen, or to a pharmaceutical composition according to the invention, for the preparation of a medicament for treating cancer in a subject.

It finally relates to a method for treating in a subject a cancer, wherein a therapeutically effective amount of an anti-LSP1 antibody conjugated to an antigen, preferably a cancer antigen, or of a pharmaceutical composition according to the invention, is administered to said subject suffering from a cancer.

In a particular embodiment, the invention also concerns an in vitro method for selecting a subject for a treatment with an anti-LSP1 antibody conjugated to a drug or with a pharmaceutical composition according to the invention or for predicting the efficacy of a treatment with an anti-LSP1 antibody conjugated to a drug or with a pharmaceutical composition according to the invention, wherein the method comprises:

(a) measuring the quantity of cells stained by an anti-LSP1 antibody according the invention in a biological sample from said subject, (b) measuring the quantity of total dendritic cells in the same sample, (c) determining the proportion of inflammatory dendritic cells in relation to total dendritic cells in said sample, (d) selecting subjects with a proportion of cells stained in their biological sample higher than at least 10%, preferably 5%, more preferably 1%, still more preferably 0.5%, even more preferably 0.1%, for a treatment with an anti-LSP1 antibody conjugated to a drug or with a pharmaceutical composition according to the invention.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present invention will be described in the following examples, which should be regarded as illustrative and not limiting.

EXAMPLES

Results

In order to identify new markers for human inflammatory dendritic cells (DC), the inventors performed a phage display screen. They sorted cells from tumor ascites into dendritic cells and non-dendritic cells (which included macrophages, other immune cells and tumor cells). First, non-dendritic cells were used to deplete the phage library, then the remaining phages were incubated with ascites dendritic cells. Hits were then screened using ascites cells from different donors. This process resulted in the discovery of antibody D4 which has a sequence of SEQ ID NO: 8.

Figure 2:
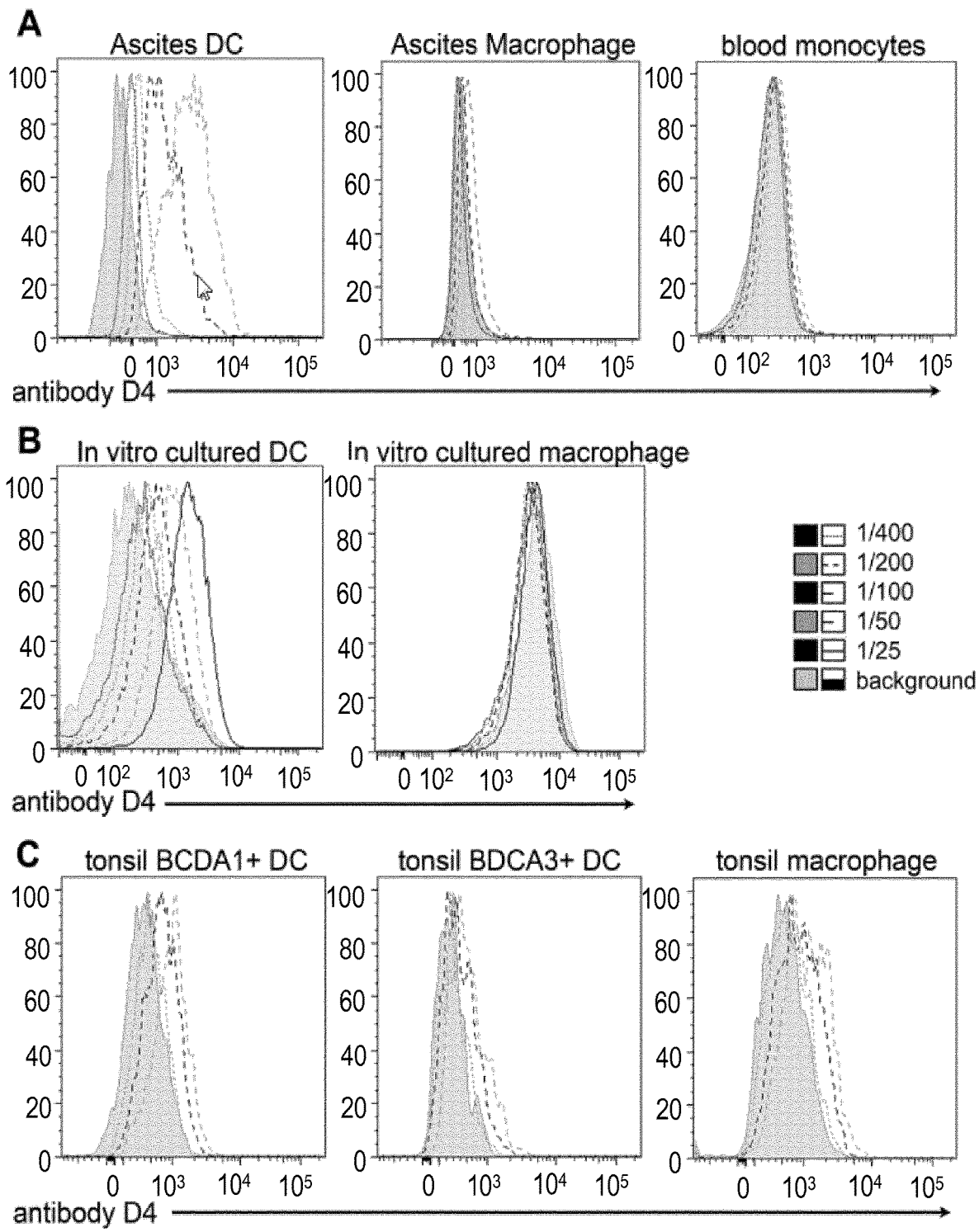
FIG. 2: Antibody D4 recognizes human inflammatory dendritic cells. (A) Cells from tumor ascites were stained with anti-CD11c, HLA-DR, BDCA1, CD16 and several dilutions of antibody D4 (initial concentration: 5 mg/mL). Ascites dendritic cells (DC) are gated as CD11c+HLA-DR+BDCA1+CD16− and ascites macrophages as CD11c+HLA-DR+BDCA1−CD16+. Blood CD14+ monocytes were isolated from total PBMC and stained with several dilutions of antibody D4. (B) In vitro equivalents of inflammatory DC and macrophages were derived in vitro from monocytes. Cells were stained with several dilutions of antibody D4. (C) Cells from tonsils were stained with anti-CD11c, HLA-DR, BDCA1, BDCA3, CD14 and several dilutions of antibody D4. BDCA1+DC are gated as CD11c+HLA-DR+BDCA1+CD14−, DCA3+DC are gated as CD11c+HLA-DR+BDCA1−CD14−BDCA3+ and macrophages as CD11c+HLA-DR+BDCA1-CD14+.

Antibody D4 stains ascites dendritic cells in a dose-dependent manner, but do not stain macrophages from the same ascites, nor blood monocytes (cf. FIG. 2A), suggesting that antibody D4 is able to stain inflammatory dendritic cells.

Figure 1:
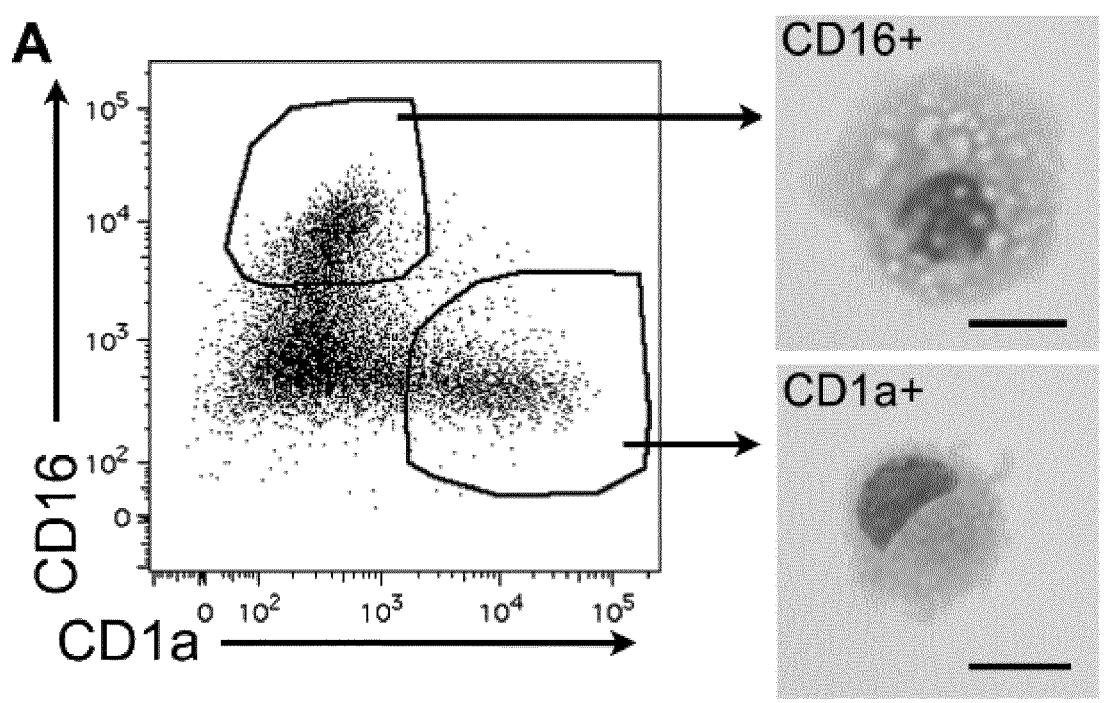
FIG. 1: Monocytes cultured with MCSF, IL-4 and TNFa yield DC and macrophages that closely resemble inflammatory DC and macrophages found in vivo. Purified blood $CD14^+$ monocytes were cultured with MCSF, IL-4 and TNFa for 5 days. (A) Sorted $CD1a^+$ and $CD16^+$ cells were analyzed after cytospin and Giemsa/May-Grünwald staining. Bar=10 μm. (B) Purified blood $CD14^+$ monocytes were cultured for 5 days with MCSF, IL-4 and TNFa, or GM-CSF and IL-4. Cells were analyzed by flow cytometry and compared to DC and macrophages present in tumor ascites (tissue mo-DC and mo-Mac). Grey shaded histograms represent isotype control stainings. (C) Transcriptomic analysis of DC and macrophages differentiated in MCSF, IL-4 and TNFa (n=6), DC differentiated in GM-CSF and IL-4 (n=6), DC and macrophages from tumor ascites (n=5), blood $CD14^+$ monocytes (n=4) and blood $CD1c^+$ DC (n=4). Hierarchical clustering representing the 1000 most variant genes. D #=donor #.

To confirm it, the inventors used in vitro equivalents of inflammatory dendritic cells. The inventors developed a novel in vitro culture system mimicking the differentiation of inflammatory dendritic cells and macrophages in the same culture. Purified blood monocytes cultured with M-CSF, IL-4 and TNF-α yield 2 main populations expressing CD16 or CD1a and displaying the features of macrophages or dendritic cells respectively (FIG. 1A). These cells have a phenotype (FIG. 1B) and transcriptome (FIG. 1C) that are very similar to those of inflammatory dendritic cells and macrophages that are found in tumor ascites. In particular, the monocyte-derived dendritic cells differentiated with M-CSF, IL-4 and TNF-α are much closer to inflammatory dendritic cells than monocyte-derived dendritic cells differentiated with the classical protocol (GM-CSF and IL-4). Then, they tested antibody D4 on these populations of in vitro inflammatory dendritic cells and macrophages. Antibody D4 stains inflammatory dendritic cells in a dose-dependent manner but do not stain macrophages from the same culture (cf. FIG. 2B). These results confirm that antibody D4 is able to stain inflammatory dendritic cells.

To assess whether antibody D4 was specific for inflammatory dendritic cells, the inventors used cells from tonsils. Antibody D4 stains BDCA1+ dendritic cells very weakly, and do not stain BDCA3+ dendritic cells nor macrophages (cf. FIG. 2C). These results show that antibody D4 recognizes specifically human inflammatory dendritic cells.

Figure 3:
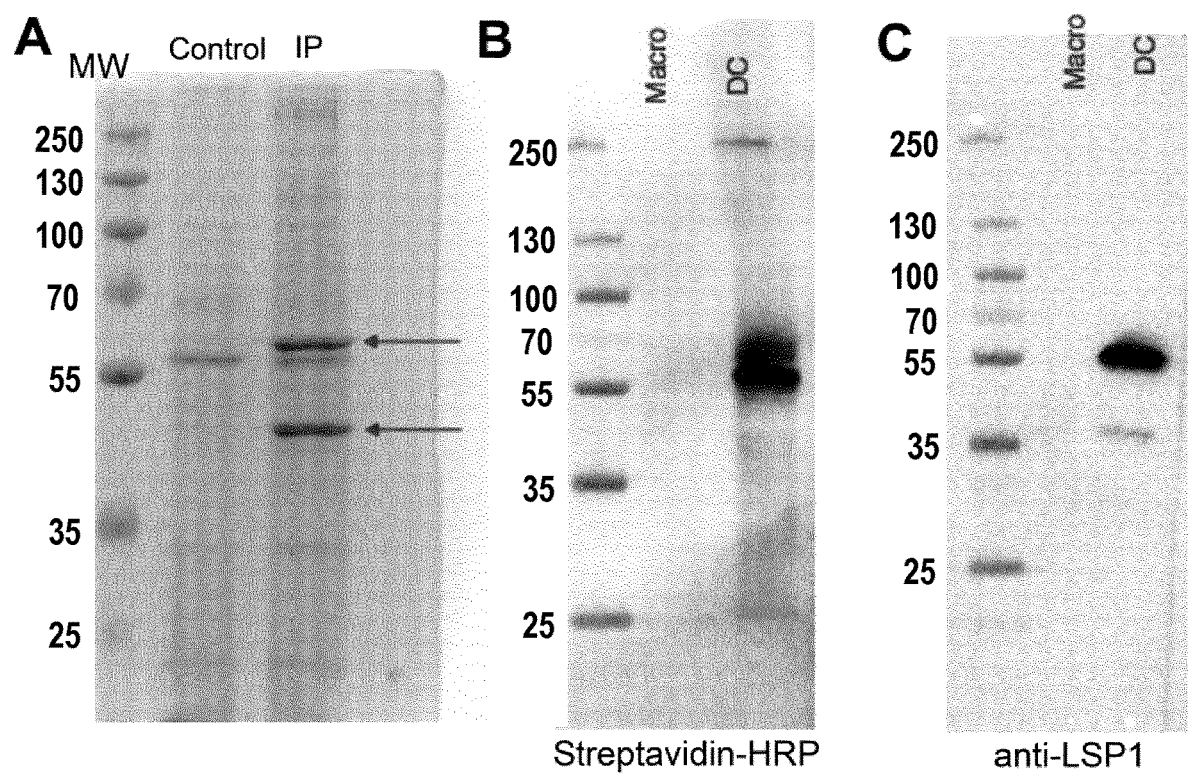
FIG. 3: Identification of LSP-1 as the target of antibody D4. (A) After incubation with D4, in vitro equivalents of inflammatory DC were lysed. Immuno-precipitation was performed on cell lysate by immuno-precipitating the C-terminal tag (streptavidin-binding peptide). Immuno-precipitated material, or control cell lysate, was loaded on a gel. After migration, proteins were revealed using Coomassie Blue. Two specific bands were identified (blue arrows).

In order to identify the target of antibody D4, the inventors performed an immunoprecipitation followed by mass-spectrometry (cf. FIG. 3A). Mass spectrometry identified the immuno-precipitated protein as "lymphocyte-specific protein 1" (LSP1), a protein thought to be cytosolic. To confirm this result, the inventors immuno-precipitated the target of antibody D4 and then stained the Western blot membrane with a commercial anti-LSP1 antibody, using streptavidin as a control (cf. FIG. 3B-3C). These results confirmed that the protein recognized by antibody D4 at the surface of inflammatory dendritic cells is LSP1.

In order to determine if commercially available anti-LSP1 antibodies can stain the surface of inflammatory dendritic cells and thus can be used to specifically stain inflammatory dendritic cells, the inventors performed flow cytometry experiments using a biotin-labelled commercial anti-LSP1 polyclonal antibody (NBP1-74048B, Novus Biologicals). This commercial anti-LSP1 antibody do not stain the surface of inflammatory dendritic cells, on the opposite to antibody D4 (cf. FIG. 3A-3B). However, when cells are fixed and permeabilized, commercial anti-LSP1 antibody is able to stain the cells in a dose-dependent manner (cf. FIG. 4C). These results show that antibody D4 recognizes an epitope that is not recognized by commercially available anti-LSP1 antibodies.

In addition, in order to determine if commercially available anti-LSP1 antibody TPD153 (monoclonal antibody) can stain the surface of inflammatory dendritic cells and thus can be used to specifically stain inflammatory dendritic cells, the inventors performed flow cytometry experiments using an Alexa647-labelled commercial anti-LSP1 TPD153 antibody (NBP2-50479AF647, Novus Biologicals). This commercial anti-LSP1 antibody does not stain the surface of inflammatory dendritic cells, as opposed to antibody D4 (cf. FIG. 5A-5B). However, when cells are fixed and permeabilized, commercial anti-LSP1 TPD153 antibody is able to stain the cells (cf. FIG. 5C). These results show that antibody D4 recognizes an epitope that is not recognized by commercially available anti-LSP1 TPD153 antibody.

Collectively, these results show that antibody D4 specifically recognizes a form of LSP1 specifically expressed at the surface of inflammatory dendritic cells.

Material and Methods

Samples Sources.

Samples of ovarian or breast tumor ascites from untreated patients were obtained from Hôpital de l'Institut Curie (Paris) in accordance with hospital guidelines. Buffy coats from healthy donors were obtained from Etablissement Français du Sang (Paris) in accordance with INSERM ethical guidelines. Tonsils from healthy patients undergoing tonsillectomy for obstructive sleep apnea were obtained from Hôpital Necker (Paris, France) in accordance with hospital ethical guidelines.

Cell Isolation and Culture.

Tumor ascites cells were isolated after centrifugation on a Ficoll gradient (Lymphoprep, Greiner Bio-One) followed by cell sorting on a FACSAria instrument (BD Biosciences). Tonsil samples were cut into small fragments, digested with 0.1 mg/mL Liberase TL (Roche) in the presence of 0.1 mg/mL DNAse (Roche) for 40 minutes at room temperature before addition of 10 mM EDTA. Cells were filtered on a 40 μm cell strainer (BD Falcon) and washed. Light density cells were isolated by centrifugation on a Ficoll gradient (Lymphoprep, Greiner Bio-One). DCs were enriched by depletion of cells expressing CD3, CD15, CD19, CD56 and CD235a using antibody-coated magnetic beads (Miltenyi). Peripheral Blood Mononuclear Cells (PBMC) were prepared by centrifugation on a Ficoll gradient (Lymphoprep, Greiner Bio-One). Blood $CD14^+$ monocytes were isolated from healthy donors' PBMC by positive selection using magnetic beads (Miltenyi). Monocytes were 97-98% CD14+CD16− as assessed by flow cytometry. Monocytes (1×10⁶ cells/mL) were cultured for 5 days in RPMI-Glutamax medium (Gibco) supplemented with antibiotics (penicillin and streptomycin) and 10% Fetal Calf Serum in the presence or absence of 100 ng/mL M-CSF (Miltenyi), 100 ng/mL GM-CSF (Miltenyi), 40 ng/mL IL-4 (Miltenyi) and 5 ng/mL TNF-α (R&D Biotechne). Cell populations were isolated by cell sorting on a FACSAria instrument (BD Biosciences).

Flow Cytometry.

Cells were stained in PBS containing 0.5% human serum and 2 mM EDTA with APC anti-CD1a (Biolegend, clone HI149) or APC-Vio770 anti-CD1a (Miltenyi, clone HI149) or PE-Vio770 anti-CD1a (Miltenyi, clone HI149), FITC anti-CD16 (Biolegend, clone 3G8), APC-eFluor780 anti-HLA-DR (eBioscience, clone LN3), Pe/Cy7 anti-CD11c (Biolegend, clone Bu15), PerCP-eFluor710 anti-CD1c (eBioscience, clone L161) or APC anti-CD1c (Biolegend, clone L161), VioGreen anti-CD14 (Miltenyi Biotec), PE anti-CD11b (BD Biosciences, clone M1/70), PE anti-FcεRI (eBioscience, clone AER-37), Alexa647 anti-CD206 (Biolegend, clone 15-2), PE anti-CD163 (Biolegend, clone GHI/61), APC anti-CD226 (Miltenyi, clone DX11), APC anti-MerTK (R&D Biotechne, clone 125518), PE anti-CD141 (Miltenyi, clone AD5-14H12), PE anti-CD88 (Biolegend, clone S5/1), APC anti-CD1b (eBioscience, clone eBioSN13), PE anti-CD64 (Biolegend, clone 10.1), biotinylated anti-CD172a (Biolegend, clone SE5A5), biotinylated anti-LSP1 (Novus Biologicals), or D4 antibody, followed by staining with APC or PE streptavidin (eBioscience), or isotype-matched control antibodies. In some experiments, cells were fixed and permeabilized using Cytofix/Cytoperm kit according to the manufacturer's instructions (BD Biosciences). Cells were analyzed on a FACSVerse (BD Biosciences) instrument. Data was analyzed with FlowJo (Tree Star).

Morphological Analysis.

Cells were subjected to cytospin and colored with May-Grunwald/Giemsa staining. Pictures were taken with a CFW-1308C color digital camera (Scion Corporation) on a Leica DM 4000 B microscope.

Affymetrix Micro-Array.

RNA was extracted using the RNAeasy Micro Kit (Qiagen) according to the manufacturer's protocol. For each condition, 100 ng of polysomal-bound RNA were employed to synthesize double-stranded cDNA using two successive reverse-transcription reactions according to the standard Affymetrix protocol. Labelled DNA was hybridized on the Affymetrix human Gene ST1.1, an oligonucleotide 28,000-gene microarray processed on an Affymetrix GeneTitan device. The raw data were preprocessed using the RMA (Robust Multi-array Average) method available in oligo package Gene expression levels were analyzed on a base-2 logarithmic scale. Moderated t-tests were performed using the limma package and the p-values were corrected for multiple testing with the Benjamini Hochberg method. Probe set were considered as statistically differentially expressed if associated adjusted p-value was lower than 5%. The hierarchical clustering (HC) was computed with the pvclust package in R provides p-values for HC based on multiscale bootstrap resampling. The analysis was performed in two steps. First, samples were grouped in "in vitro" (IL34 mo-Mac, IL34 mo-DC, M-CSF mo-Mac, M-CSF mo-DC, GM-CSF mo-DC) or "ex vivo" (monocytes, ascites mo-Mac, ascites mo-DC, CD1c+ DC) datasets, and genes which were only expressed in one group were excluded from the analysis. In the second step, only the 1000 most variants genes based on IQR were used for the HC. The HC analysis was conducted with number of bootstrap 10000, using Pearson's correlation coefficient and average linkage method.

Western Blot.

Cells were lysed in RIPA buffer (Thermo Scientific) supplemented with complete Mini EDTA-free protease inhibitor cocktail (Roche). Post-nuclear lysates were resolved by SDS-PAGE using 4-12% BisTris NuPAGE gels (Invitrogen) and proteins were transferred to membranes (Immunoblot PVDF membranes, Bio-Rad). Membranes were stained with anti-LSP1 (Novus Biologicals), D4 antibody, or streptavidin-HRP staining (Pierce). In some experiments, gels were stained with Coomassie Blue (Thermo Fisher).

Phage Library.

Details on the phage library can be found in patent WO2015063331 A1, the disclosure of which is incorporated herein.

Phage display screen.

100 µL of supernatant (80 µL phages+20 µL PBS/human serum1%) were incubated for 1 h on ice with $1.10^5$ cells from tumor ascites. After washing, phage binding on ascites cells was detected by flow cytometry using PE anti-M13 antibody (GE healthcare), and FITC anti-CD16 (Biolegend, clone 3G8), APC-eFluor780 anti-HLA-DR (eBioscience, clone LN3), Pe/Cy7 anti-CD11c (Biolegend, clone Bu15), PerCP-eFluor710 anti-CD1c (eBioscience, clone L161). Cells were analyzed on a FACSVerse (BD Biosciences) instrument. Data was analyzed with FlowJo (Tree Star).

Immunoprecipitation.

All the incubation steps were performed rocking the tubes constantly. Cleared cell lysates resuspended in an equal volume of IP buffer (10 mM Tris-HCl, pH 8.0, 150 mM NaCl, 1% NP40) were pre-incubated 1 h at 4° C. in the presence of 200 µL of protein G agarose beads (Thermo Fisher) and successively washed 3 times in IP buffer to eliminate unspecific binding. The supernatant was recovered by centrifugation (3 min×2500 g), mixed with 200 µg of antibody, and incubated 2 h at 4° C. Finally, 200 µL of washed protein G agarose beads were added and washed after 1 h at 4° C. 5 times in 10 mL of IP buffer five times before being resuspended in 50 µL of SDS loading buffer and heated 10 min at 95° C.

Mass-Spectrometry.

Gel slices were washed and proteins were reduced with 10 mM DTT before alkylation with 55 mM iodoacetamide. After washing and shrinking the gel pieces with 100% (vol/vol) MeCN, we performed in-gel digestion using trypsin (Roche) overnight in 25 mM $NH_4HCO_3$ at 30° C. Peptides were analyzed by LC-MS/MS using an Ultimate 3000 system (Dionex) coupled to an LTQ-Orbitrap XL mass spectrometer (Thermo Fisher Scientific). Proteins were denatured, reduced, alkylated and digested with trypsin. A nanoflow HPLC instrument (Ultimate 3000, Dionex) was coupled on-line to the LTQ-Orbitrap XL Hybrid Ion Trap-Orbitrap mass spectrometer (Thermo Scientific) and an RSLCnano system (Ultimate 3000, Thermo Scientific) to the Orbitrap Fusion Tribrid mass spectrometer (Thermo Scientific). Peptides were loaded onto a C18-reversed phase column (300-µm inner diameter×5 mm; Dionex), separated and MS data acquired using Xcalibur software. Peptides were separated by HPLC over a two-step gradient of 157 min from 0% to 30% (vol/vol) acetonitrile and of 20 min [from 30% to 50% (vol/vol)] and by UHPLC over a two-step gradient of 100 min [from 5% to 35% (vol/vol)] and of 15 min from 35% to 75% (vol/vol) acetonitrile (75-µm inner diameter×50 cm; C18 PepMap, Dionex) and analyzed in the Orbitrap XL or Orbitrap Fusion mass spectrometer (Thermo Scientific). Full-scan MS was acquired with 60,000 and 120,000 resolution in the Orbitrap analyzer, respectively and ions from each full scan were fragmented with CID or HCD, respectively and analyzed in the linear ion trap. For identification, the data were searched against the UniProtKB-SwissProt human database using Mascot 2.3 (Matrix Science) through Proteome Discoverer 1.4 (Thermo Scientific) workflow editor tool. All peptide/protein identification data were processed using the Institut Curie-developed software myProMS which performs search engine results validation, false-positive rate (FDR)-based data filtering, protein quantification, statistical analysis, and data visualization.

The invention claimed is:

1. An anti-LSP1 (Leukocyte specific protein 1) single domain antibody comprising a variable domain that comprises three CDRs (complementarity determining regions), the first CDR (CDR1) consisting of SEQ ID NO: 1, the second CDR (CDR2) consisting of SEQ ID NO: 2 and the third CDR (CDR3) consisting of SEQ ID NO: 3.

2. The anti-LSP1 single domain antibody according to claim 1, wherein the anti-LSP1 single domain antibody is a humanized single domain antibody.

3. The anti-LSP1 single domain antibody according to claim 1, wherein said single domain antibody comprises the sequence FR1-CDR1-FR2-CDR2-FR3-CDR3-FR4 and wherein FR1, FR2, FR3 and FR4 are framework regions or humanized framework regions of a VHH.

4. The anti-LSP1 single domain antibody according to claim 3, wherein the VHH comprises camelized or llamaized framework regions of a human VH.

5. The anti-LSP1 single domain antibody according to claim 3, wherein:
FR1 consists essentially of an amino acid sequence of SEQ ID NO: 4;
FR2 consists essentially of SEQ ID NO: 5;
FR3 consists essentially of SEQ ID NO: 6; and/or
FR4 consists essentially of SEQ ID NO: 7.

6. The anti-LSP1 single domain antibody according to claim 1, wherein said single domain antibody is a single domain antibody that comprises SEQ ID NO: 8.

7. The anti-LSP1 single domain antibody according to claim 1, wherein said single domain antibody is labelled or fused to a detection entity.

8. The anti-LSP1 single domain antibody according to claim 1, wherein said single domain antibody is conjugated to a drug or to an antigen.

9. The anti-LSP1 single domain antibody according to claim 8, wherein the drug is a cytotoxic drug or an anti-inflammatory drug.

10. A pharmaceutical composition comprising a single domain antibody according to claim 8 and at least one pharmaceutically acceptable excipient.

11. A method for treating a subject with an inflammatory pathology comprising administering an antibody according to claim 8, or a pharmaceutical composition comprising said antibody to a subject having an inflammatory pathology.

12. The anti-LSP1 single domain antibody according to claim 3, wherein:
CDR1 consists of SEQ ID NO: 1;
CDR2 consists of SEQ ID NO: 2;
CDR3 consists of SEQ ID NO: 3;
FR1 consists essentially of SEQ ID NO: 4;
FR2 consists essentially of SEQ ID NO: 5;
FR3 consists essentially of SEQ ID NO: 6; and
FR4 consists essentially of SEQ ID NO: 7.

13. An in vitro method for diagnosing inflammatory pathologies in a subject comprising of staining inflammatory dendritic cells in a biological sample from said subject with an anti-LSP1 antibody according to claim 1 that is labeled or fused to a detection entity.

14. The method according to claim 13, wherein the label or detection entity is a radiolabel, an enzyme label, a fluorescent label, a biotin-avidin label, a tag or a chemiluminescent label.

15. A method of selecting a subject for a treatment with an anti-inflammatory drug or for predicting the efficacy of a treatment with an anti-inflammatory drug in a subject comprising:
(a) measuring the quantity of cells stained by an anti-LSP1 antibody according to the claim 1 in a biological sample from said subject,
(b) measuring the quantity of total dendritic cells in same sample,
(c) determining the proportion of inflammatory dendritic cells versus total dendritic cells in said sample,
(d) selecting subjects with a proportion of cells stained in their biological sample that is higher than at least 0.1% for a treatment with an anti-inflammatory drug, said antibody being labeled or fused to a detection entity.

16. The method according to claim 15, wherein the label or detection entity is a radiolabel, an enzyme label, a fluorescent label, a biotin-avidin label, a tag or a chemiluminescent label.

17. A method of specifically binding inflammatory dendritic cells with an antibody comprising contacting inflammatory dendritic cells with an antibody according to claim 1.

18. A method of purifying inflammatory dendritic cells comprising contacting a biological sample comprising inflammatory dendritic cells with an antibody according to claim 1 and separating said inflammatory dendritic cells to which said antibody is bound from other cells in said biological sample.

19. A method of immunostaining inflammatory dendritic cells comprising contacting inflammatory dendritic cells with an antibody according to claim 1, said antibody being labeled of fused to a detection entity.

20. The method according to claim 19, wherein the label or detection entity is a radiolabel, an enzyme label, a fluorescent label, a biotin-avidin label, a tag or a chemiluminescent label.

21. A method of imaging inflammatory dendritic cells in vivo comprising administering an antibody according to claim 1 to a subject, contacting inflammatory dendritic cells in said subject, and imaging the subject to detect inflammatory dendritic cells, said antibody being labeled.

22. The method according to claim 11, wherein the drug is a cytotoxic drug or an anti-inflammatory drug.

* * * * *

```
                          SEQUENCE LISTING

<160> NUMBER OF SEQ ID NOS: 8

<210> SEQ ID NO 1
    <211> LENGTH: 7
    <212> TYPE: PRT
    <213> ORGANISM: Artificial Sequence
    <220> FEATURE:
    <223> OTHER INFORMATION: CDR1

<400> SEQUENCE: 1

Arg Thr Ser Tyr His Asp Asn
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: CDR2

<400> SEQUENCE: 2

Arg Tyr Ala Asn Thr Lys Ser
    1               5

<210> SEQ ID NO 3
    <211> LENGTH: 12
    <212> TYPE: PRT
    <213> ORGANISM: Artificial Sequence
    <220> FEATURE:
    <223> OTHER INFORMATION: CDR3

<400> SEQUENCE: 3

Tyr Gly Pro Val Gly Trp Trp Arg Gly Gly Thr Pro
    1               5                   10

<210> SEQ ID NO 4
    <211> LENGTH: 28
    <212> TYPE: PRT
    <213> ORGANISM: Artificial Sequence
    <220> FEATURE:
    <223> OTHER INFORMATION: FR1

<400> SEQUENCE: 4

Met Ala Glu Val Gln Leu Gln Ala Ser Gly Gly Gly Phe Val Gln Pro
    1               5                   10                  15

Gly Gly Ser Leu Arg Leu Ser Cys Ala Ala Ser Gly
                20                  25

<210> SEQ ID NO 5
    <211> LENGTH: 19
    <212> TYPE: PRT
    <213> ORGANISM: Artificial Sequence
    <220> FEATURE:
    <223> OTHER INFORMATION: FR2

<400> SEQUENCE: 5

Met Gly Trp Phe Arg Gln Ala Pro Gly Lys Glu Arg Glu Phe Val Ser
    1               5                   10                  15
```

```
Ala Ile Ser

<210> SEQ ID NO 6
<211> LENGTH: 39
<212> TYPE: PRT
<213> ORGANISM: Artificial Sequence
<220> FEATURE:
<223> OTHER INFORMATION: FR3

<400> SEQUENCE: 6

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 7
<211> LENGTH: 12
<212> TYPE: PRT
<213> ORGANISM: Artificial Sequence
<220> FEATURE:
<223> OTHER INFORMATION: FR4

<400> SEQUENCE: 7

Tyr Trp Gly Gln Gly Thr Gln Val Thr Val Ser Ser
1               5                   10

<210> SEQ ID NO 8
<211> LENGTH: 124
<212> TYPE: PRT
<213> ORGANISM: Artificial Sequence
<220> FEATURE:
<223> OTHER INFORMATION: Antibody D4

<400> SEQUENCE: 8

Met Ala Glu Val Gln Leu Gln Ala Ser Gly Gly Gly Phe Val Gln Pro
1               5                   10                  15

Gly Gly Ser Leu Arg Leu Ser Cys Ala Ala Ser Gly Arg Thr Ser Tyr
            20                  25                  30

His Asp Asn Met Gly Trp Phe Arg Gln Ala Pro Gly Lys Glu Arg Glu
        35                  40                  45

Phe Val Ser Ala Ile Ser Arg Tyr Ala Asn Thr Lys Ser Tyr Tyr Ala
    50                  55                  60

Asp Ser Val Lys Gly Arg Phe Thr Ile Ser Arg Asp Asn Ser Lys Asn
65                  70                  75                  80

Thr Val Tyr Leu Gln Met Asn Ser Leu Arg Ala Glu Asp Thr Ala Thr
                85                  90                  95

Tyr Tyr Cys Ala Tyr Gly Pro Val Gly Trp Trp Arg Gly Gly Thr Pro
            100                 105                 110

Tyr Trp Gly Gln Gly Thr Gln Val Thr Val Ser Ser
        115                 120
```